United States Patent
Jakus et al.

(10) Patent No.: US 11,896,740 B2
(45) Date of Patent: Feb. 13, 2024

(54) WATER-SOLUBLE SALT PARTICLE CONTAINING COMPOSITIONS AND POROUS MATERIALS MADE THEREFROM

(71) Applicant: Northwestern University, Evanston, IL (US)

(72) Inventors: Adam E. Jakus, Chicago, IL (US); Ramille N. Shah, Oak Brook, IL (US); Nicholas R. Geisendorfer, Chicago, IL (US)

(73) Assignee: NORTHWESTERN UNIVERSITY, Evantson, IL (US)

( * ) Notice: Subject to any disclaimer, the term of this patent is extended or adjusted under 35 U.S.C. 154(b) by 0 days.

(21) Appl. No.: 16/760,355

(22) PCT Filed: Nov. 27, 2018

(86) PCT No.: PCT/US2018/062595
§ 371 (c)(1),
(2) Date: Apr. 29, 2020

(87) PCT Pub. No.: WO2019/108531
PCT Pub. Date: Jun. 6, 2019

(65) Prior Publication Data
US 2020/0353129 A1    Nov. 12, 2020

Related U.S. Application Data

(60) Provisional application No. 62/591,336, filed on Nov. 28, 2017.

(51) Int. Cl.
| | |
|---|---|
| A61L 27/56 | (2006.01) |
| A61L 27/18 | (2006.01) |
| A61L 27/44 | (2006.01) |
| C08J 9/26 | (2006.01) |
| C08L 67/04 | (2006.01) |

(52) U.S. Cl.
CPC .............. A61L 27/56 (2013.01); A61L 27/18 (2013.01); A61L 27/446 (2013.01); C08J 9/26 (2013.01); C08L 67/04 (2013.01); C08J 2201/03 (2013.01); C08J 2201/0444 (2013.01); C08J 2207/10 (2013.01); C08J 2367/04 (2013.01)

(58) Field of Classification Search
CPC ........ A61L 27/56; A61L 27/18; A61L 27/446; C08J 9/26; C08J 2201/03; C08J 2201/0444; C08J 2207/10; C08J 2367/04; C08L 67/04
See application file for complete search history.

(56) References Cited

U.S. PATENT DOCUMENTS

| | | | |
|---|---|---|---|
| 6,562,374 B1 | 5/2003 | Han et al. | |
| 10,584,254 B2 * | 3/2020 | Shah | ..................... B29C 64/165 |
| 2009/0075382 A1 | 3/2009 | Sachlos | |
| 2015/0037385 A1 | 2/2015 | Shah et al. | |
| 2017/0081534 A1 * | 3/2017 | Shah | ..................... C09D 11/104 |
| 2018/0273720 A1 * | 9/2018 | Huang | .................. B29C 64/165 |

FOREIGN PATENT DOCUMENTS

| | | |
|---|---|---|
| CN | 103910901 A | 7/2014 |
| JP | 01089486 A | 4/1989 |
| JP | 05098576 A | 4/1993 |
| JP | 2002-514253 A | 5/2002 |
| WO | 9844027 A1 | 10/1998 |

OTHER PUBLICATIONS

Mar. 15, 2019 International Search Report for PCT/US2018/062595.
Mar. 15, 2019 Written Opinion of International Searching Authority for PCT/US2018/062595.
Adam E. Jakus et al., "Hyperelastic 'Bone': A Highly Versatile, Growth Factor-Free, Osteoregenerative, Scalable, and Surgically Friendly Biomaterial," *ScienceTranslationalMedicine* vol. 8 Issue 358 (Sep. 28, 2016).
Adam E. Jakus et al., "Robust and Elastic Lunar and Martian Structures From 3D-Printed Regolith Inks," *Scientific Reports* vol. 7 No 44931 (Mar. 20, 2017).
Soumyaranjan Mohanty et al., "Fabrication of Scalable Tissue Engineering Scaffolds with Dual-Pore Microarchitecture by Combining 3D Printing and Particle Leaching," *Material Science and Engineering C: Materials for Biological Applications* vol. 61 pp. 180-189 (Dec. 19, 2015).
Krebs, Melissa D., et al. "Injectable poly (lactic-co-glycolic) acid scaffolds with in situ pore formation for tissue engineering." Acta biomaterialia5.8 (2009): 2847-2859—14 pages.
Partial Supplementary European Search Report for EP18882937.8 dated Nov. 16, 2021—15 pages.
Extended European Search Report issued in European Patent Application No. 18882937.8 dated Feb. 17, 2022, 12 pages.
Examination Report for European Patent Application No. 18882937.8 dated Feb. 17, 2023, 8 pages.
Second Official Action for Japanese Patent Application No. 2020-528405 dated Mar. 1, 2023, 8 pages.

* cited by examiner

Primary Examiner — Robert A Wax
Assistant Examiner — Olga V. Tcherkasskaya
(74) Attorney, Agent, or Firm — Hahn Loeser & Parks LLP

(57) ABSTRACT

Compositions for forming porous materials and three-dimensional objects, including fibers, films and coatings made from the materials are provided. Also provided are methods for forming the porous objects from the compositions. The compositions include a solvent, a polymer binder that is soluble in the solvent, and solid particles that are insoluble in the solvent. The solid particles include water-soluble salt particles that can be selectively dissolved from objects made from the compositions to render the resulting structures porous.

20 Claims, 15 Drawing Sheets

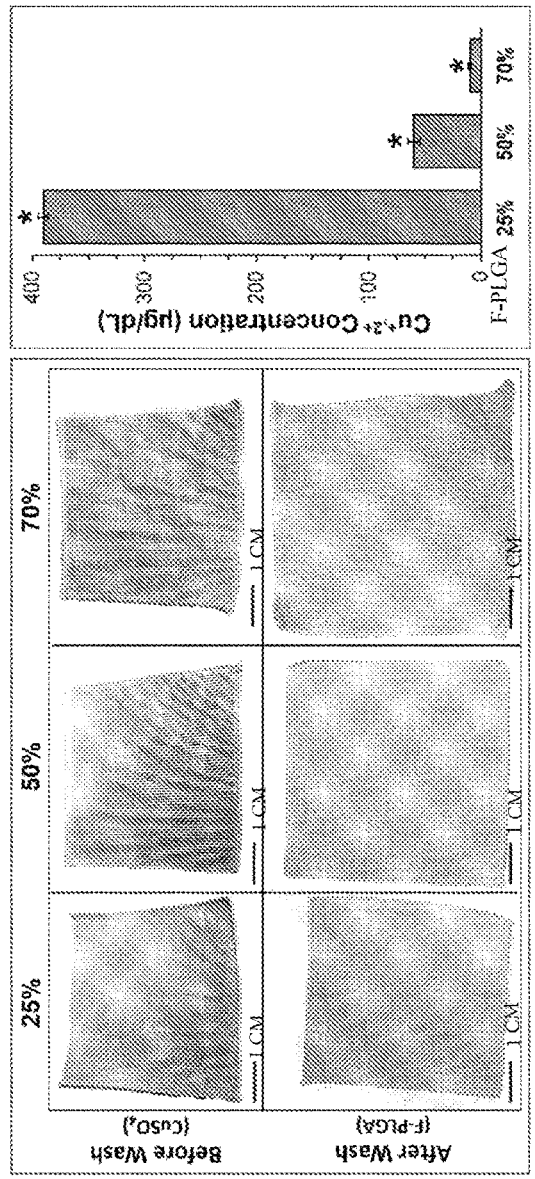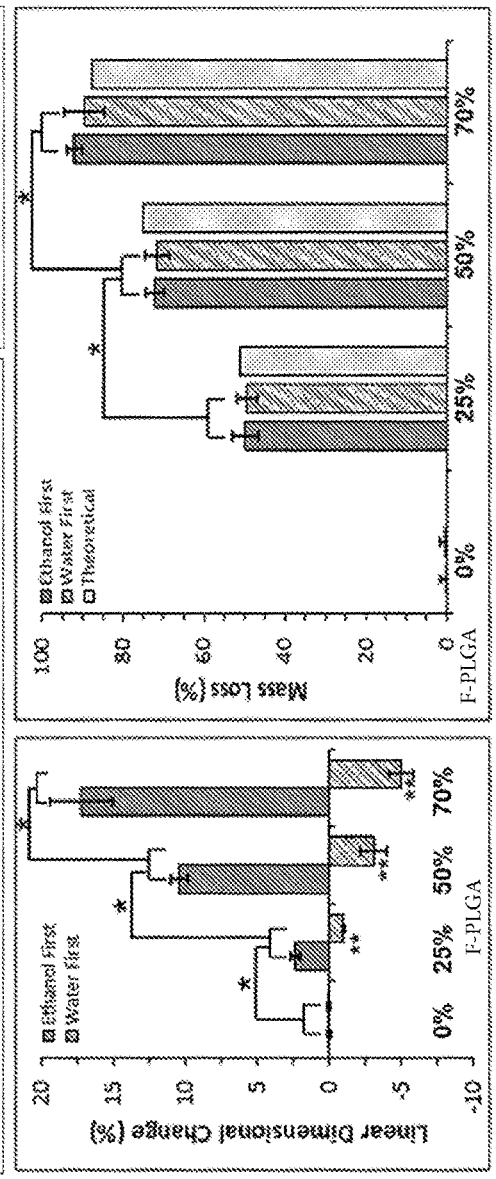
FIG. 3A FIG. 3B FIG. 3C FIG. 3D

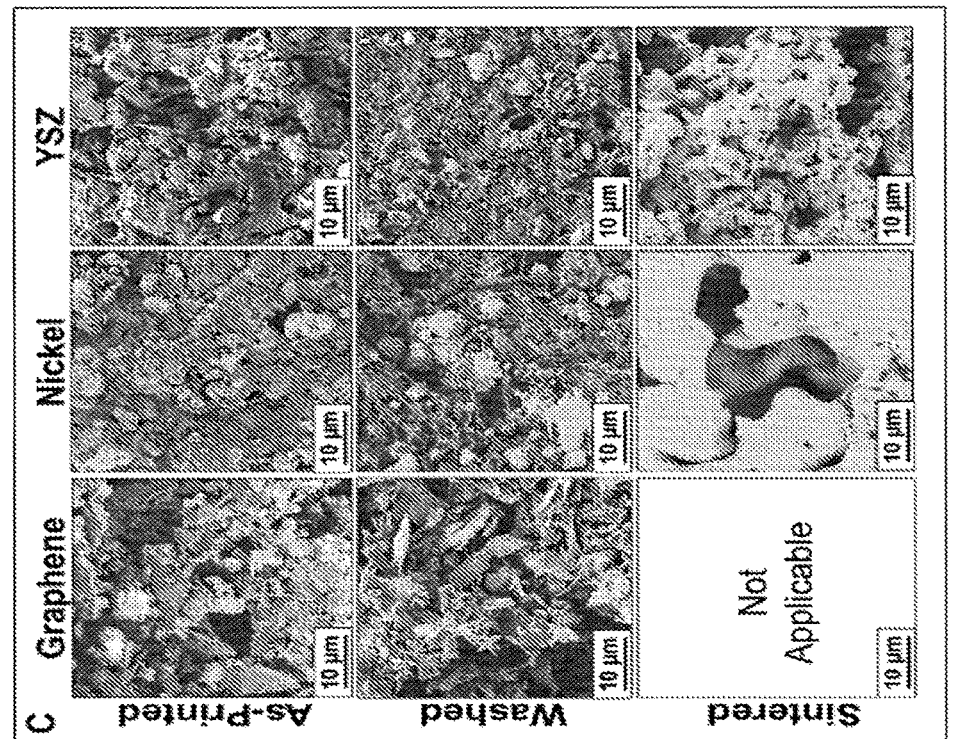
FIG. 9C
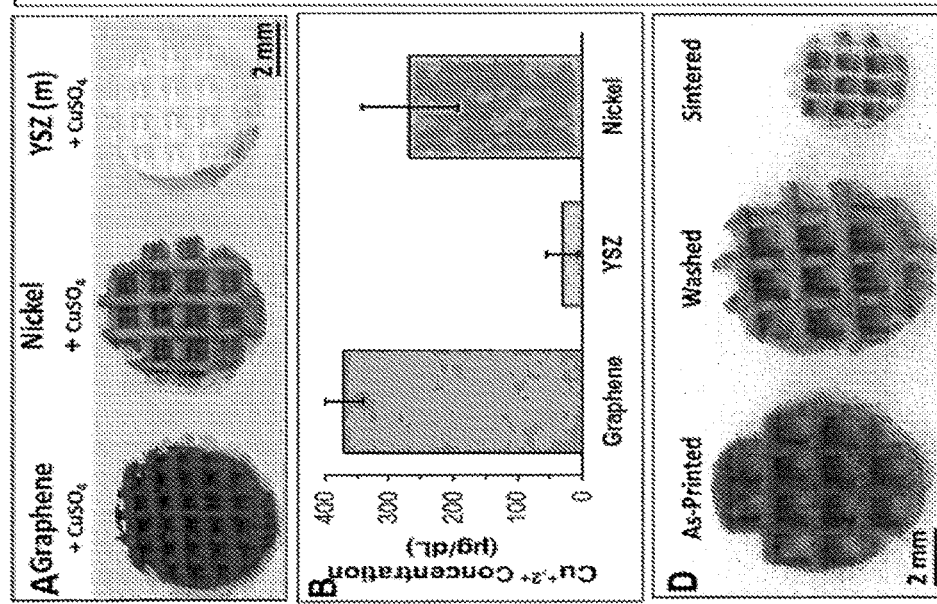
FIG. 9A
FIG. 9B
FIG. 9D

WATER-SOLUBLE SALT PARTICLE CONTAINING COMPOSITIONS AND POROUS MATERIALS MADE THEREFROM

CROSS-REFERENCE TO RELATED APPLICATIONS

The present application is a submission under 35 U.S.C. § 371 of international application no. PCT/US2018/062595, filed 27 Nov. 2018 and published in the English language with publication no, WO 2019/108531 A1 on 6 Jun. 2019, which claims priority to U.S. provisional patent application No. 62/591,336, that was filed Nov. 28, 2017, the entire contents of which are hereby incorporated by reference.

BACKGROUND

Regardless of the material system—metal, ceramic, polymer, biologic, composite, etc.—porosity is a major, defining structural characteristic that can substantially influence the mechanical, physical, chemical, and biological properties and performance of a material or a device. For example, elevated porosity in a material can decrease stiffness relative to its fully dense counterpart, while simultaneously increasing gravimetric strength. As porosity increases, so too does the total surface area per unit weight of that material, which may be desirable for catalytic or electrochemical systems, such as batteries, solid oxide fuel cells, and additional applications that depend on surface mediated catalysis and reactions. From a biological perspective, porosity in biomaterials, such as polymers or biologics, has been demonstrated to be critical for adequate tissue integration, implant acceptance, and overall biofunctionality regardless of the target tissue or organ. These examples are just a few of the many positive implications of porosity and demonstrate the importance of this characteristic in influencing the properties and performance of many types of materials across a diverse range of applications and fields.

This important role of porosity has led researchers to spend decades working to develop effective manufacturing and modelling approaches and methodologies that produce materials and structures with defined, engineered porosities across a variety of length scales—often referred to as hierarchical porosity. Depending on the scientific or engineering field, the name given to particular pore forming processes and the resulting structure can vary ("scaffold," "cellular solid," "foam," etc.), but several major methods include foaming, freeze-casting, freeze-drying (also known as lyophilization), dissolution based leaching, and solid-state porogen thermal decomposition. Through the alteration of various process-specific parameters, the nature of the engineered porosity, such as total porosity, pore size, size distribution, and shape can be influenced, but not precisely controlled across the totality of the resulting object. To introduce larger scale (millimeter-to-centimeter), controlled porosity within materials and fabricated structures, additional processes are utilized, such as extrusion, and more recently, additive manufacturing and 3D-printing.

SUMMARY

Methods for forming porous three-dimensional (3D) materials and objects formed from the materials, including fibers, films and coatings, are provided.

One embodiment of a method of forming a porous material includes the steps of: (a) forming a material comprising: a polymer binder; and solid particles, wherein the composition comprises at least about 20 vol. % of solid particles based on its solids content and at least some of the solid particles are water-soluble salt particles; (b) exposing the material to a salt-hydrating solution, such as an aqueous alcohol solution, wherein the water-soluble salt particles are hydrated, but not dissolved, and undergo a volume increase; and (c) dissolving at least a portion of the hydrated, water-soluble salt particles in water, thereby leaving pores in the material.

Hydration of the salt particles, without substantial dissolution, results in a large volumetric increase of the salt particles and the material itself while retaining the original form of the material. The hydrated salt particles can then be removed by dissolution in water, leaving open pores in the material that are larger than the original salt particles. As a result, the pore volume in the porous material is greater than it would be if salt particles that did not undergo hydration were used.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIGS. 3A-3D. A) Image series showing 3D-printed 25, 50, and 70% 5 cm-square sheets before ($CuSO_4$; as-printed) and after salt-leaching (F-PLGA), washing (70% ethanol before water), and lyophilization. Note that scale bars are equivalent for all images (1 cm). B) Average concentrations of copper remaining in 25, 50, and 70% F-PLGA 3D-printed samples after leaching/washing (ethanol wash first). C) Average linear dimensional change and D) mass loss of 3D-printed 25, 50, and 70% $CuSO_4$ structures after having been leached/washed in 70% ethanol followed by water (EthanolFirst) or water followed by 70% ethanol (Water First). D) also denotes theoretical maximum mass loss of each material group based on mass ratio of PLGA to $CuSO_4$ used to create each material. Error bars denote standard deviation from average. * in B) and C): $p \leq 0.05$ between compositional groups with same washing conditions. ** in C) $p \leq 0.05$ between same compositional groups and different washing conditions. * in D); $p \leq 0.05$.

FIGS. 9A-9E. A) Images of samples punched from larger squares 3D-printed from compound compositions composed of graphene+$CuSO_4$, nickel metal+$CuSO_4$, and YSZ+$CuSO_4$. B) Residual copper ion concentration in compound graphene, nickel metal, and YSZ 3D-printed materials after washing (ethanol wash first). C) Scanning electron micrographs of the interior cross-sections of compound graphene, nickel metal, and YSZ 3D-printed fibers as-printed, after washing/leaching (ethanol first), and sintering. Note that only the compound nickel metal and YSZ specimens were sintered. Sintering is not relevant for graphene. D) Photograph illustrating color and size of compound nickel samples as-printed, after leaching/washing, and after sintering. E) Linear dimensional change of compound graphene (Gr), nickel metal (Ni), and YSZ samples resulting from washing (ethanol) and subsequent sintering. Note that graphene was not sintered; thus, linear dimensional change for sintered graphene is not applicable.

DETAILED DESCRIPTION

Figure 1A:
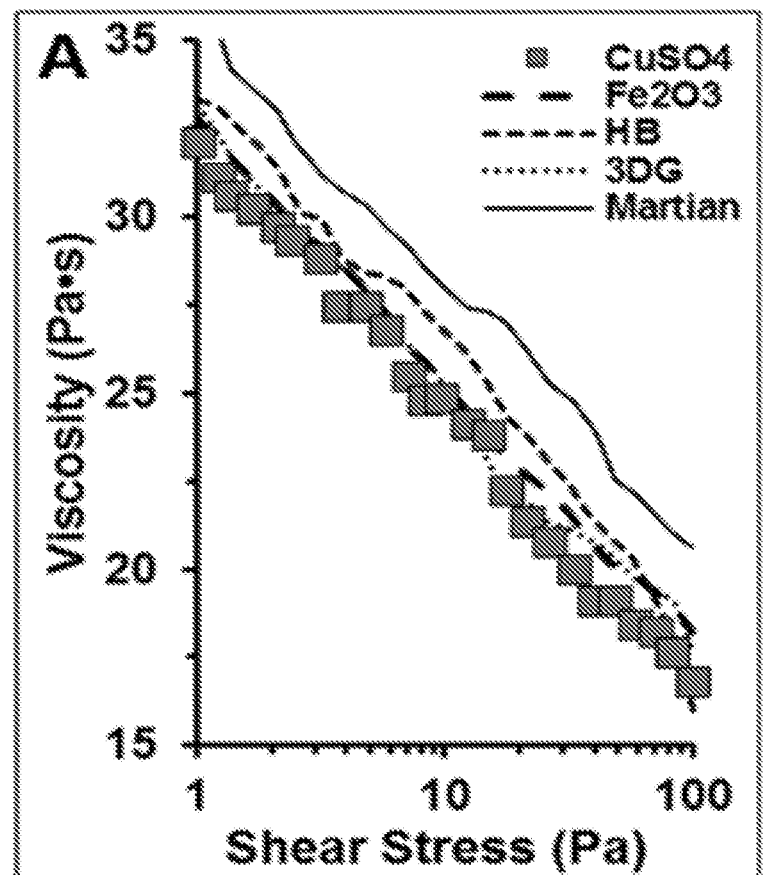
FIGS. 1A-1D. A) Viscosity as a function of shear stress of 70% by volume (vol. %) $CuSO_4$ composition, which is one embodiment of a porous material in accordance with disclosure, in comparison with previously reported, direct extrusion 3D-Printed related $Fe_2O_3$, Hyperelastic "Bone" (HB), 3D-Graphene (3DG), and Martian regolith (Martian) compositions. (See, A. E. Jakus, et al., Advanced Functional Materials 2015, 25, 6985; A. E. Jakus, et al., Science translational medicine 2016, 8, 358ra127; A. E. Jakus, et al., ACS Nano 2015, 9, 4636; and A. E. Jakus, et al., Scientific Reports 2017.) B) Image of a 4×4×4 cm cube being 3D-printed from 70 vol. % $CuSO_4$ composition via direct, room temperature extrusion 3D-printing. C) Schematic illustrations and D) corresponding images outlining the process and stages for creating high porosity polylactic-co-glycolic acid ("PLGA"; also known as polylactide-co-glycolide, "PLG") from 3D-printed $CuSO_4$. Prior to leaching/washing, the materials are referred to as 25, 50, and 70% $CuSO_4$, where the % refers to vol. %. After washing, the materials are referred to 25, 50, and 70% F-PLGA, respectively. As-printed, the $CuSO_4$ materials are gray/light blue in color, but transition to bright blue upon exposure to water and dissociation of the comprising $CuSO_4$ salt. Complete dissolution of the $CuSO_4$ salt from the material into surrounding aqueous media is indicated by a color transition from blue to bright white. E) Image of an as-received PLGA granule and equivalent mass F-PLGA structure from 3D-printed 70% $CuSO_4$ after leaching and lyophilization.

Compositions for forming porous materials and 3D objects, including fibers, films and coatings made from the materials, are provided. Also provided are methods for forming the materials and the porous 3D objects from the compositions. Cell culture scaffolds, tissue and organ growth scaffolds made from the porous materials are also provided. In addition, methods for incorporating liquids and hydrogels into the porous materials are also provided The compositions contain: a solvent; a polymer binder that is soluble in the solvent; and solid particles that are insoluble in the solvent, wherein the solid particles include water-soluble salt particles. The water-soluble salt particles can be selectively dissolved from objects made from the compositions to render the resulting structures porous. The porous structures have uses in a broad range of applications where highly porous materials are desirable, including tissue growth and engineering, thermoelectrics, bioelectronics, batteries and fuel cells, catalysis, optical guides, and filters.

In some embodiments of the methods, the water-soluble salt particles can be hydrated in the presence of a water-alcohol solution, such that their volume is increased via hydration prior to their dissolution in water. Once the salt is removed, the resulting polymer structures are almost entirely porous and contain very little solid material by volume.

Some of the compositions are characterized in that they can be 3D printed via room-temperature extrusion into self-supporting fibers that form self-supporting 3D objects and architectures. Self-supporting strands and structures formed by 3D printing the compositions are characterized in that they substantially retain the 3D shape imparted to them by the extrusion process. For this reason, the compositions may be referred to as "3D printable compositions." In addition, the 3D printed objects may be removed from the substrate upon which they are 3D printed, while remaining structurally intact. As such, the compositions differ from ink compositions used in two-dimensional (2D) printing (e.g., inkjet printing) to form very thin films of text, or patterns on the surface of a substrate. Once the fibers have been extruded, the water-soluble salt particles can be removed by dissolution in water or an aqueous solution, leaving open pores in the fibers.

The compositions generally comprise small volume fractions of the polymer binder. In some embodiments of the composition, the polymer binder is an elastic polymer (elastomer). The use of elastic polymer binders promotes the robustness of objects, films and coatings formed from the compositions. In addition, when the compositions are extruded, the elastic polymer binders provide for the formation of extruded stands that are continuous, flexible and strong. This enables 3D printing of architectures with complex and unsupported features and of scaffold structures having mechanical properties that render them well-suited for use in culturing biological cells and/or growing biological tissues. Moreover, 3D structures formed from the compositions can adopt, at least in part, the elastomeric properties of the elastic polymer binders. Thus, some embodiments of materials and objects that are formed from the compositions have strongly elastic mechanical properties which allow them to 'bounce back' to their original shape after undergoing loading (e.g., compression or tension). By way of illustration, fibers, coatings, films or other objects made from compositions that use elastic polymer binders can have tensile elastic moduli of at least 2 MPa, at least 50 MPa, and at least 100 MPa.

The polymers provide a binder that helps to hold the particles together in the final printed or deposited fiber, film or coating. The polymers should be soluble or substantially soluble in the solvent at the intended printing temperature, but are desirably insoluble or substantially insoluble in water at the intended printing temperature, or at higher temperatures. Depending on the intended application of the materials and objects that are to be formed from the compositions, the polymer binders may be biodegradable and/or biocompatible elastic polymers. Elastic polymers may comprise, for example, a polyester, a polymethacrylate, a polyacrylate, a polyethylene glycol, polycarbonate, polystyrene, polyurethane, or a combination of two or more thereof. Examples of suitable polyester polymers that can be included in the compositions are polylactic acid (PLA), glycolic acid, copolymers of PLA and glycolic acid (i.e., polylactic-co-glycolic acid (PLGA)), and polycaprolactone (PCL). Some embodiments of the compositions comprise blends of one or more of these polyesters with other polyesters or with one or more non-polyester elastomeric polymers. For applications that do not require biocompatibility and/or biodegradability, other polymers, such as polystyrene can be used.

In some of the compositions, water-soluble salt particles are the only solid particles in the compositions, while in other compositions the water-soluble salt particles are mixed with water-insoluble solid particles. The water-soluble salts should be sufficiently soluble in water that they can be selectively solubilized over a time period and temperature range at which the other components of the fibers, coatings, or films, (e.g., the polymer binders and other solid particles) are not solubilized. By way of illustration, salts having a water solubility of at least 100 g/L at room temperature can be used. However, salts with lower water solubilities can also be used. Examples of water-soluble salts that can be included in the compositions include inorganic metal salts, such as copper-containing salts. Other water-soluble salts include water-soluble nitrates and sulfates (including copper sulfate), chlorides, bromides, and iodides; as well as water-soluble carbonates (including sodium carbonate, potassium carbonate, and ammonium carbonate) and hydroxides (including sodium hydroxide, potassium hydroxide, and ammonium hydroxide). The salt component can also be a mixture of any of two or more of the above-mentioned the salts.

In addition to the water-soluble salt particles, the solid particles in the composition can optionally include a broad range of other types of particles that are insoluble or substantially insoluble in the solvent and in water. The additional solid particles include covalent solids, ionic solids, and metallic solids. For example, the solid particles may be ceramic particles (e.g., metal oxides and oxides of non-metal elements or non-water soluble metal compounds, such as non-water soluble metallic salts), metal particles, metal alloy particles, organic (e.g., polymer) particles, magnetic particles, carbon particles (e.g., carbon nanotubes, graphene flakes or powders and graphite), water-insoluble salt particles (e.g., water-insoluble sulfates, fluorides, chlorates, carbonates), natural soil particles (e.g., planetary soils particles), and naturally occurring particles derived from biological sources (e.g., decellularized extracellular matrix (ECM) particles and mammalian and plant proteinaceous particles) or any combination of these—including mixtures of inorganic particles with organic particles. Some such particles may be biological in origin (e.g., decellularized extracellular matrix, proteins, or drugs). The ceramic particles may be complex ceramics. For the purposes of this disclosure, a complex ceramic is an ionic solid with a single crystalline structure under any given condition and is comprised of multiple cationic, anionic, or cationic and anionic species. A bioceramic is defined as a ceramic that is suitable for biological applications (i.e., it is non-toxic and biocompatible) or a ceramic having a composition that is naturally produced by living organisms.

In some embodiments of the materials, the composition includes bioactive ceramic particles. As used herein, the term bioactive ceramic refers to a material which is capable of promoting the growth of new tissue, such as osteo, chondral or osteochondral tissue. In addition to comprising a bioactive material, the ceramic particles are desirably also relatively stiff, capable of promoting cell adhesion, and are osteoinductive, osteoconductive and/or chondrogenically active. Some embodiments of the bioactive ceramics support osteogenesis and chondrogenesis under specific differentiation media conditions. That is, they can be both chondrogenically and osteogenically active. Hydroxyapatite (HAp) is an example of a suitable bioactive ceramic from which the bioactive ceramic particles can be composed. HAp is a bioactive ceramic and the native mineral component of natural bone. HAp has osteoconductive properties, which provide it with the capacity to induce the growth of new, natural bone on and around the material, as well as biochemically promoting new bone formation. Other calcium phosphates, such as tricalcium phosphate (TCP) are additional examples of bioactive ceramics that can be included in the compositions. Other examples include calcium carbonates, calcium sulfates, silicates, and silicon compounds.

The materials and, therefore, the fibers, coatings, films, and other objects formed from the compositions, are characterized by high particle loadings. For example, some embodiments of the compositions have a solid particle content of at least 50 vol. % based on the solids content of the composition. For compositions that do not include any solids, other than the polymer binder, the water-soluble salt particles, and, optionally, other solid particles, the solids content is determined by the total amount of polymer binder and particles in the composition, without taking the solvent into account. This includes embodiments of the compositions that have a solid particle content of at least 60 vol. %, at least 80 vol. % and at least 90 vol. %, based on the solids content of the composition. The ratio of water-soluble salt particles to other particles in the compositions will depend on the desired degree of porosity in the objects made from the compositions. By way of illustration only, in various embodiments of the compositions 1% to 99% of the solid particles are water-soluble salt particles and 99% to 1% of the solid particles are non-water-soluble particles. This includes embodiments in which 20% to 80% of the solid particles are water-soluble salt particles and 80% to 20% of the solid particles are non-water-soluble particles, and further includes embodiments in which 40% to 60% of the solid particles are water-soluble salt particles and 60% to 40% of the solid particles are non-water-soluble particles.

The solid particles may have a broad range of sizes and shapes, including both regular, symmetric shapes and irregular shapes. For example, they may be substantially spherical (i.e., spherical or very close to spherical allowing for some imperfections; e.g., nanospheres or certain irregularly-shaped granules), elongated cylindrical (e.g., fibers, nanowires, and nanorods), plate-like (e.g., sheets, flakes and platelets) with dimensions in the range from 10 nm (or smaller) to one mm (or larger). For example, the water-soluble salt particles and/or other particles may have diameters of at least about 10 nm, at least about 20 nm, at least about 100 nm, at least about 0.5 µm, and at least about 1 µm. The size of the water-soluble salt particles will affect the size of the pores in the materials and, therefore, also the fibers, coatings, films and other objects made from the materials. Therefore, the selected particle size will depend on the intended application of the objects. By way of illustration, for compositions used to make cell culture scaffolds, water-soluble salt particles having dimensions in the range from about 0.5 µm to about 10 µm, including in the range from about 1 µm to 5 µm, may be used. As used herein, the term "solid particles" refers to particles that comprise a solid material, as opposed to a liquid (e.g., a droplet). However, the "solid particles" need not be completely solid throughout their interior. For example, "solid particles" includes porous particles and hollow particles.

The solvent can be a mixture of two or more organic co-solvents, in which case the solvent is referred to as a solvent system. Solvent systems include graded solvents that include a primary organic solvent that has a high vapor pressure, and therefore evaporates rapidly, at room temperature (23° C.) and atmospheric pressure (101.3 kPa). The graded solvent system further includes one or more additional organic solvents having lower vapor pressures than the primary solvent at room temperature. Suitably high vapor pressures at room temperature and atmospheric pressure include those in the range from about 20 kPa to about 60 kPa, which includes those in the range from about 25 kPa to about 55 kPa. Moreover, if printing is carried out at pressures lower than atmospheric pressure, other lower volatility solvents could be used.

Some embodiments of the solvent systems comprise dichloromethane (DCM) as a primary solvent, which may be used in combination with one or more additional organic solvents. The use of DCM is advantageous because, upon extrusion of the composition, DCM, which is a very high volatility solvent, evaporates very rapidly, leaving a solid, continuous fiber. Chloroform is another example of a suitable primary organic solvent. The primary solvent is the majority solvent in the solvent system. That is, it accounts for at least 50% by volume (vol. %) of the solvents in the solvent system. In some embodiments, the primary organic solvent accounts for at least 70 vol. % of the solvent system. This includes embodiments in which primary organic solvent accounts for at least 90 vol. % of the solvent system.

The additional organic solvents desirably have vapor pressures that are lower than that of DCM at the desired printing or deposition temperature (e.g., room temperature—about 23° C.). As a result, the additional organic solvents evaporate more slowly over time, but permit adjacent layers to merge together during deposition, resulting in a single, monolithic structure with strong interlayer adhesion and fidelity. Some embodiments of the solvent systems comprise an additional solvent that is a surfactant, an additional solvent that is a plasticizer, or a combination of at least two additional solvents—one of which is a surfactant and the other of which is a plasticizer. 2-butoxyethanol (2-Bu), dibutylphthalate (DBP), and glyceryl triacetate (also known as triacetin) are examples of additional organic solvents that may be included in the solvent system. In solvent systems comprising DBP, the DBP acts as a plasticizer. However, other organic plasticizers, such as glyceryl triacetate, can be used in place of, or in combination with, the DBP. In solvent systems comprising 2-Bu, the 2-Bu acts as a surfactant. However, other organic surfactants can be used in place of, or in combination with, the 2-Bu. Some of the compositions consist essentially of, or consist only of, a primary solvent, a second solvent that acts as a plasticizer and a third solvent that acts as a surfactant. For example, some of the compositions consist of, or consist essentially of, DCM, 2-Bu and DBP. For compositions comprising both a plasticizer and a surfactant, the preferred mass ratio of the plasticizer to the surfactant will depend, at least in part, on the printing or coating conditions and the equipment being used. By way of illustration only, in some embodiments of the solvent systems, the molar ratio of plasticizer to surfactant (e.g., DBP to 2-Bu) is in the range from about 1:1 to about 4:1. This includes embodiments in which the molar ratio is in the range from about 1:2 to about 2:1.

The compositions can be made simply by mixing the solvent, the binder polymers, the water-soluble salt particles and, optionally, other solid particles to form a composition. The compositions can be used to form a variety of three-dimensional objects, films and coatings using a variety of deposition methods. The printing and other deposition methods can be carried out at, or near, room temperature and ambient pressure. Typically, the printing temperature will be from about 20° C. up to about 40° C. However, printing can be carried out at higher or lower temperatures—although it should generally be carried out at temperatures below the boiling points of the solvent. The amount of solvent in the composition should provide it with a viscosity that is suitable for the intended method of deposition. If excess solvent is needed in order to solubilize the polymer, the excess solvent can be allowed to evaporate until the composition has achieved a viscosity suitable for deposition. Thus, the compositions may initially take the form of a viscous liquid. Suitable viscosities will depend on the intended method of deposition and the deposition equipment (e.g., nozzle diameter in the case of 3D printing). For example, if the composition is intended for use as a 3D printable composition, it should have a viscosity suitable for 3D printing via extrusion through a print nozzle. By way of illustration only, some embodiments of the compositions that are suitable for 3D printing have a viscosity in the range from about 25 Pa·s to about 100 Pa·s at room temperature, including in the range from about 25 Pa·s to about 50 Pa·s at room temperature. For coating applications, such as spin coating and dip coating, the viscosities are generally lower, typically in the range from about 1 Pa·s to about 5 Pa·s at room temperature. Due to its simplicity, this composition formulation process is highly scalable. Quantities as small as, for example, a few milliliters or as large as, for example, many gallons or tons may be produced.

The compositions can be used to print objects using a 3D printer and layer-by-layer deposition, where a 3D printer is a printer capable of direct extrusion of a composition through a nozzle upon the application of pressure (e.g., via mechanical or pneumatic pressure) to the composition at or near room-temperature, which is held in a container (e.g., a syringe or print head) that is in fluid communication with the nozzle. This type of printing is sometimes referred to as "Direct Ink Writing" (DIW). In one embodiment of a printing process, the composition is loaded into a syringe or syringe-like reservoir a 3D printer and extruded onto a substrate through the orifice in one or more print nozzles via pneumatic or mechanical pressure. Upon extrusion, solvents in the solvent system evaporate and a solid, continuous fiber is formed. The overall architectures of the layer-by-layer printed objects can be previously defined through computer aided design (CAD) or other three-dimension digital data. The substrates upon which the objects can be printed are not limited by, but may depend on, the nature of the object being printed and its intended application. Illustrative examples of suitable substrate materials include glass, metal, plastics, paper, sandpaper, semiconductors, dielectrics and ceramics.

Other non-extrusion-based methods for depositing the compositions include coating the compositions onto a substrate and allowing the solvents in the solvent system to evaporate. Suitable coating processes include painting a composition onto a substrate and coating a substrate with a composition via, for example, dip coating or spin coating. For example, the compositions can be used to create thin, particle-laden films via dip coating or can be used to coat existing bulk objects. Thicker coatings can be built up on a substrate using multiple dip coating steps to form a multi-layered coating. These coatings can comprise multiple layers formed from the same composition or from different compositions. Doctor blading and molding of the compositions can also be used.

Once a fiber, coating, film, or other object has been formed, the water-soluble salt particles can be leeched from the object by solubilizing them with an aqueous solution. This can be accomplished, for example, by simply submerging the object in water or an aqueous solution. The water-soluble salt particles need not be completely removed from the object. However, those that are leave behind pores that render the objects porous.

In some embodiments of the methods, the materials can be washed with a salt-hydrating solution, such as solution comprising water and an alcohol, before the water-soluble salt particles are solubilized with in water. This salt-hydrating solution, which does not significantly solubilize the salt particles, hydrates the salt, resulting in a salt volume increase and, as a result, a volumetric expansion of the structure, relative to a structure obtained without the intermediate alcohol-water washing step, as discussed in greater detail in the Example. Ethanol, isopropyl alcohol, and mixtures thereof can be used in the salt-hydrating solution. Other alcohols can be used, provided that the salt particles chosen are highly soluble in water, but have a low solubility in the alcohol-water solution. By way of illustration, the exposure to the salt-hydrating solutions can be continued for time and/or at temperatures that provide a salt particle volume increase of 10% or more. This includes embodiments of the methods that include a salt particle volume increase of 20% or more and further includes embodiments of the methods that include a salt particle volume increase of 30% or more.

In embodiments of the methods in which the water-soluble salt particles are not completely removed for the objects, it may be advantageous to use salt particles having constituents (e.g., cations and/or anions) that do not have a negative effect on the functionality or performance of the porous objects. For example, for tissue engineering or other medical applications, biocompatible salt particles can be used. In some embodiments, the salts can be selected such that the residual cations and/or anions have a beneficial effect on the final porous object. By way of illustration, residual metal ions, such as copper ions, from water-soluble metal salt particles can enhance the anti-bacterial properties and/or vascularization of an object. Thus, in some embodiments of objects, such as tissue growth scaffolds, made using a water-soluble copper containing salt, the object has a residual copper content in the range from about 1 to about 200 µg/dL. This includes objects having a residual copper content in the range from about 1 to about 100 µg/dL and in the range from about 5 to about 60 µg/dL. Methods of measuring the copper content of the materials are described in Example 1.

Finally, the porous object can be dried by, for example, lyophilization. If the final object contains solid particles and it is desired to remove part or all of the polymer binder from the final object, the object can be sintered to bind the solid particles and remove some or all of the polymer binder.

The porosity of fibers, coatings, or films made using the methods will depend on the water-soluble salt particle content of the compositions from which they are made and the extent of water-soluble salt particle leeching. However, by using highly water-soluble salts and a high salt particle concentration, objects with high porosities can be fabricated. By way of illustration, fibers, coatings and/or films, made by the methods can have a porosity of at least 50%, at least 60%, at least 80%, at least 90%, and at least 95%. This includes porosities in the range from 60% to 98% and from 80% to 95%. Methods of measuring porosity are discussed in the Example.

Optionally, some or all of the pores in the highly porous structures remaining after the dissolution of the water-soluble salt particles can be back-filled with a liquid solution. In some embodiments, the liquid solution is a gel precursor solution and that precursor solution can be gelled in situ within the porous structure in order to provide a hydrogel supported within the porous structure. The nature of the gelling process will depend on the nature of the gel being formed. For example, in various embodiments of this process, thermal gelation or cross-linking gelation can be used, including physical cross-linking, ionic cross-linking, or chemical/covalent cross-linking. In some embodiments, the gel precursor solutions are aqueous solutions comprising monomers, oligomers, and/or polymers, a crosslinking agent and, optionally, a crosslinking initiator. If the hydrogels are to be used in medical or tissue engineering applications, the monomers, oligomers, and/or polymers should be biocompatible, and the precursor solution may optionally also include cells and/or a bioactive factor. The back-filling can be carried out by injecting the liquid solution into the porous material or soaking the porous material in a liquid solution.

For tissue engineering applications, the compositions can be used to fabricate cell culture scaffolds or tissue growth scaffolds, which are porous structures that permit cell integration, tissue ingrowth, and/or vascularization. The use of 3D printing for the fabrication of the scaffolds is advantageous because it provides for regular geometric patterning of the layers that make up the scaffold, which makes it possible to control and tailor the porosity, pore size and pore interconnectivity of the scaffold. For example, the printed layers may comprise a plurality of printed fibers. In some embodiments, the fibers in each layer are substantially parallel to one another, while the fibers in a given layer are not oriented parallel to the fibers in other layers.

The porous scaffolds can be used as tissue growth scaffolds by seeding the scaffolds with tissue-forming cells, or cells that are precursors to tissue-forming cells. Tissue can be grown by culturing the seeded scaffolds in a cell growth culture medium. Mesenchymal stem cells, hematopoetic stem cells, embryonic stem cells, and induced pluripotent stem cells are examples of precursors to tissue-forming cells. Examples of tissue-forming cells include osteoblasts, chondrocytes, fibroblasts, endothelial cells, and myocytes. Biological cells can also be included in the liquid solutions or gels that are used to back-fill the porous materials in order to provide them with tissue-specific bioactivity.

Compositions for use in the printing or casting of cell culture or tissue growth scaffolds may optionally include one or more bioactive factors, such as genes, proteins, peptides, growth factors, pharmaceutical compounds, antibiotics, and the like that facilitate cell and tissue growth by, for example, inducing cell differentiation. Because the compositions can be formulated and printed at relatively low temperatures (e.g., room temperature), bioactive factors can be added to the formulation and, subsequently, incorporated into structures made from the compositions, without undergoing heat-induced degradation. Bioactive factors, such as genes, proteins, peptides, growth factors, pharmaceutical compounds, and antibiotics, can also be included in the liquid solutions or gels that are used to back-fill the porous materials in order to provide them with tissue-specific bioactivity.

Example 1

Beyond illustrating a salt particle-containing composition that can be rapidly 3D-printed into clinically relevant-scale architectures, it was demonstrated that by controlling the ratio of $CuSO_4$ and PLGA in the composition, the mechanical, physical, and in vitro biological properties of the resulting material structures could be tailored. Further, this work highlights the value of material processing and final porosity in biological applications, as it was demonstrated that low material porosity, 3D-printed PLGA performed poorly when seeded with adult human mesenchymal stem cells (hMSCs); while high porosity PLGA highly supported the attachment, viability, proliferation, and matrix synthesis of the exact same cell system cultured under the same conditions. Finally, it was demonstrated that this process can be applied to introduce additional porosity into other 3D-printed functional material systems including metals, ceramics, and graphene.

Results and Discussion

Salt Composition Synthesis and Material Selection

Three distinct $CuSO_4$-PLGA compositions, defined by the solids-content volumetric ratio of $CuSO_4$ to PLGA, were synthesized—70:30 (70%), 50:50 (50%), and 25:75 (25%) $CuSO_4$:PLGA. For purposes of clarity and nomenclature, the resulting compositions and as-3D-printed materials, referred to hereafter as 25, 50, or 70% $CuSO_4$, ultimately resulted in 25, 50, or 70% "Fluffy" PLGA (F-PLGA) after salt-leaching (removal of $CuSO_4$), which is described below. Briefly, anhydrous $CuSO_4$ powder was suspended in a trisolvent mixture containing dichloromethane (DCM; rapid evaporant), 2-butoxyethanol (2-Bu; surfactant), and dibutyl phthalate (DBP; plasticizer), in addition to previously dissolved, medical grade polylactide-co-glycolide (PLGA; 82:18 lactide to glycolide). Although the majority of $CuSO_4$ particles in the as-received powders were ~1-5 μm in size, larger particles and particle agglomerates were present (FIG. 2A), which would increase the likelihood of nozzle clogging during 3D-printing. To mitigate the potential for clogging, the as-received $CuSO_4$ powders were sieved through a 325 mesh, removing large particles and agglomerates (FIG. 2A), and resulting in a powder comprised of ~1-5 μm particles with particle aggregates typically no larger than 10 μm in diameter. The resulting suspensions thickened via ambient conditions or mild heating (<45° C.) and evaporation of excess DCM with periodic manual stirring in a chemical fume hood until a low-shear stress viscosity (30-35 Pa s) appropriate for 3D-printing was achieved. The 70% $CuSO_4$ compositions exhibited shear thinning behavior (FIG. 1A) appropriate for extrusion at room temperature. After synthesis, the compositions could be used immediately or stored in air-tight, glass containers at 4° C. until needed.

Although a wide variety of salt chemistries could be utilized for this process, $CuSO_4$ was specifically selected for this illustrative example, for numerous reasons. First, $CuSO_4$ is highly water soluble (320 g/L at 20° C.), allowing the rapid removal of salt from the 3D-printed structures during leaching. Second, as $CuSO_4$ is exposed to water, becomes hydrated, and dissociates into its constituent ions, $Cu^{2+}$ and $SO_4^{2-}$, there is a rapid and dramatic color change from off-white to bright blue (from $Cu^{2+}$ in solution). This obvious color change can be utilized as a visual indicator, identifying the real-time progress and degree of salt removal from the 3D-printed material. Third, because this example is targeted at biological applications of the resulting F-PLGA materials, and because it can be difficult to assure the complete removal of salt and its constituent ions from the PLGA, it is advantageous if the residual ions in the material have beneficial biologic effects. In this case, small concentrations of $Cu^2$ can not only enhance a materials' antibacterial properties, but can also promote vascularization and wound healing. Finally, $CuSO_4$ is widely available.

Figure 1B:
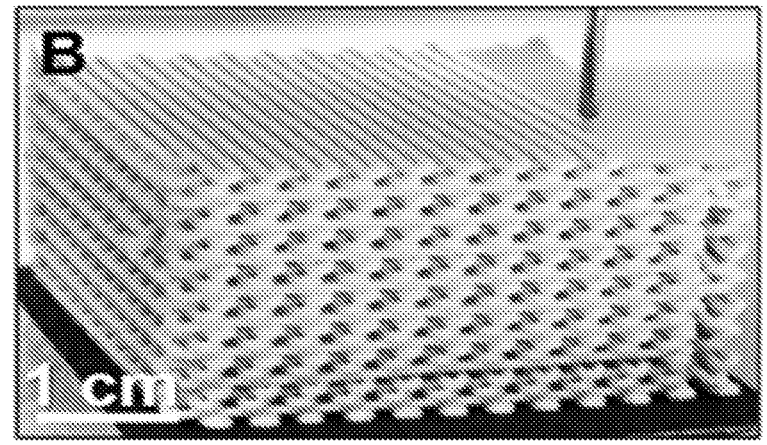

From 3D-Printed $CuSO_4$ to F-PLGA $CuSO_4$ compositions can be rapidly 3D-printed via simple room-temperature extrusion into solid objects, can be handled immediately after fabrication, do not require time to dry or any additional chemical, physical, or thermal processing to make them mechanically stable (FIG. 1B), and can be co-3D-printed with any other 3D-paint based material. Because this work focused on characterizing material properties, relatively simple geometries, similar to those shown in FIG. 1B, were created for testing. However, much more complex geometries can readily be fabricated, at linear deposition rates exceeding 100 mm/s from nozzles ranging from 200 urn to 1000 μm in diameter. As the liquid-like $CuSO_4$ composition left the nozzle, the majority solvent component, DCM, near-instantly evaporated, resulting in a rapid liquid-to-solid transition. As this occurred, small amounts of residual DCM, as well as the minority surfactant and plasticizer, which have very low vapor pressures, remained in the now-solid material, causing local dissolution and rapid precipitation of PLGA as the newly deposited material came into contact with previously deposited layer. This resulted in near-seamless fusion between 3D-printed layers.

Figures 1C, 1D:
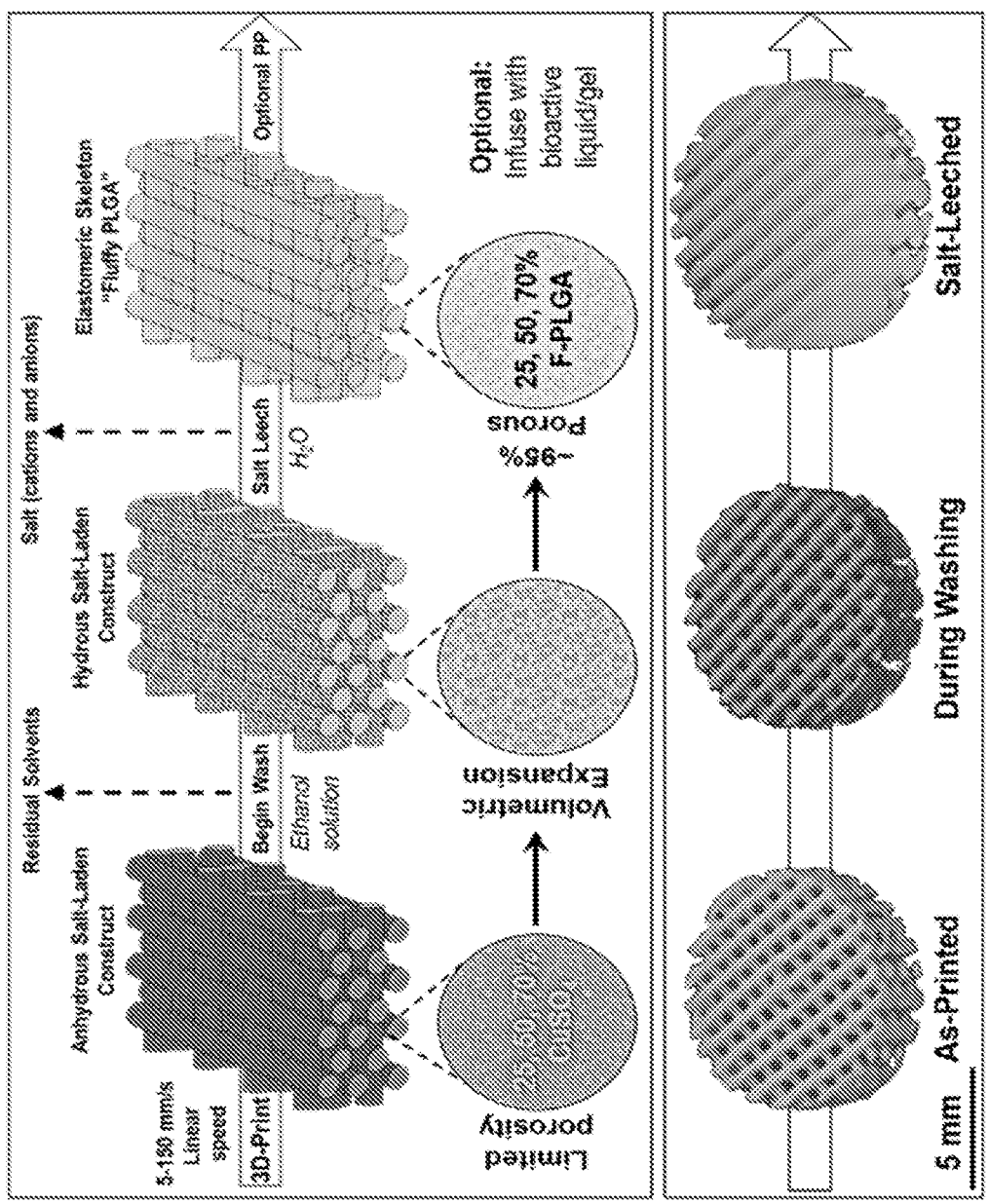
Figure 1E:
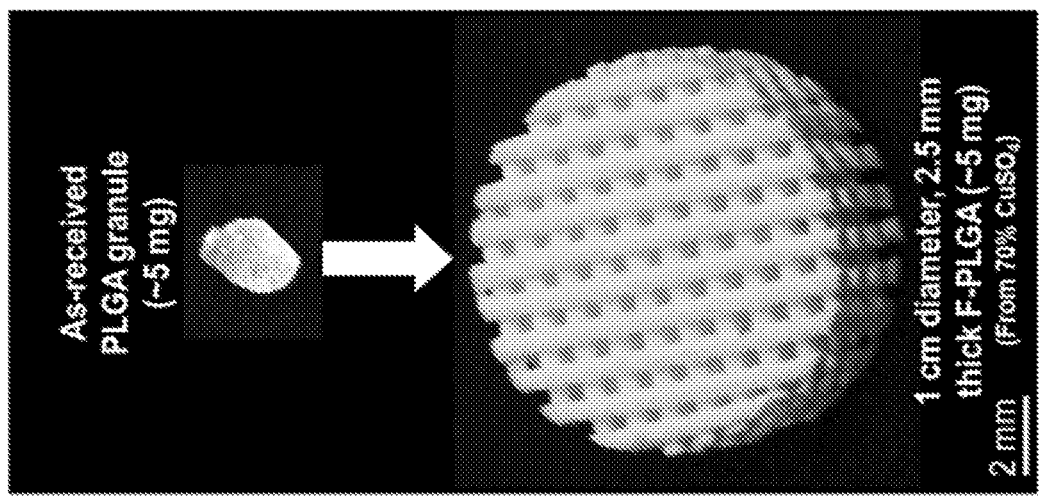

The 3D-printed $CuSO_4$ objects were transformed into their F-PLGA counterparts through the process illustrated schematically and photographically in FIGS. 1C and 1D, respectively. The water washing step hydrated the $CuSO_4$ ($CuSO_4.5H_2O$), and dissociated and solubilized the $CuSO_4$ salt and its component ions, resulting in an intermediate bright blue color transformation of the objects as the $Cu^{2+}$ ions were dissociated from the salt, but had yet to leach into the surrounding aqueous environment. The 70% ethanol step not only further sterilized the material for biological applications, but removed residual organic solvents that would otherwise be cytotoxic. The order of the washing steps can have substantial impact on the properties of the resulting material, as is discussed in detail later. After sufficient leaching and washing, the material was lyophilized to remove moisture, resulting in a highly porous PLGA framework, F-PLGA. Through this process, relatively small volumes of raw PLGA material could yield volumetrically large, but highly porous, ordered 3D-printed structures (FIG.

1E). 3D-printed CuSO$_4$ objects, as well as F-PLGA counterparts, could be cut, rolled, folded, etc. as needed.

To remove the CuSO$_4$ component as well as residual solvents from the 3D-printed objects, they were exposed to aqueous media in the form of 70% ethanol followed by sterile, deionized water. It was qualitatively observed that as CuSO$_4$ content increased, so too did the rate of salt leaching as well as the total degree of salt leaching. As can be seen in FIG. 3A, the 25, 50, and 70% CuSO$_4$ 5×5 cm sheets were originally off-white in color. After undergoing a 70% ethanol wash followed by deionized water, the CuSO$_4$ objects transformed into their respective F-PLGA counterparts. The 50 and 70% F-PLGA sheets became bright white, while the 25% F-PLGA sheet retained a light blue hue, indicating that a non-significant amount of Cu$^{2+}$ was retained within the PLGA matrix comprising the structure. This was further quantitatively verified with a Cu$^{2+}$ assay (FIG. 3B). On average, 25% F-PLGA material had 6.5 and 39 times as much residual copper ion concentration (390.2±4.5 µg/dL) than the 50% (59.3±5.4 µg/dL) and 70% (9.7±1.3 µg/dL) F-PLGA materials, respectively.

Physical Properties & Microstructure Before and after Washing

Figures 2A, 2B:
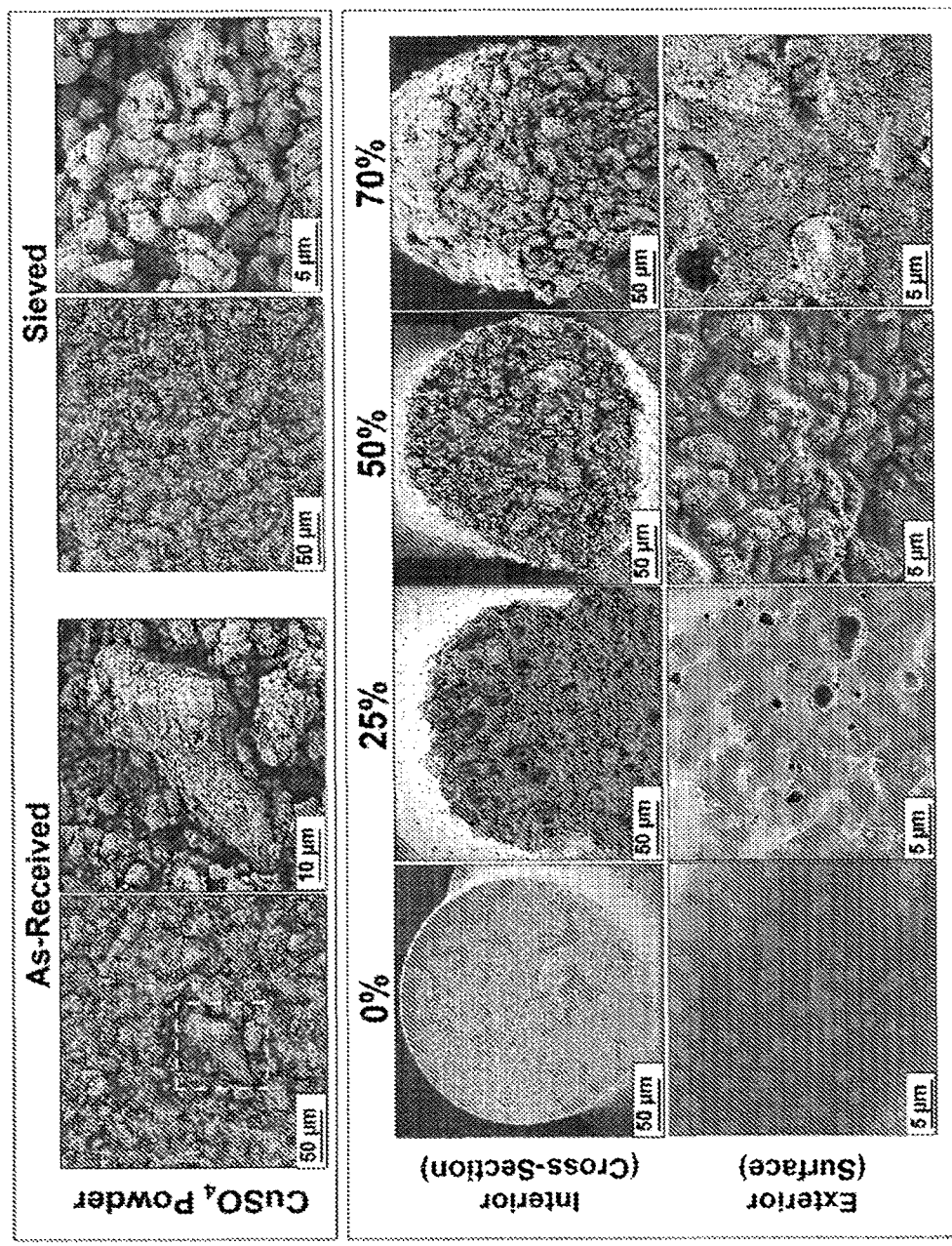
FIGS. 2A-2C. A) Scanning electron micrographs of $CuSO_4$ powders as-received (left) and after being sieved through a −325 mesh (right). B) Scanning electron micrographs of the interior cross-sections (top) and exterior surfaces (bottom) of single fibers 3D-printed from 0, 25, 50, and 70% $CuSO_4$ compositions prior to salt leaching. C) Scanning electron micrograph of a cut, salt-leached fiber of 70% $CuSO_4$, showing its unique porous microstructure.
Figure 2C:
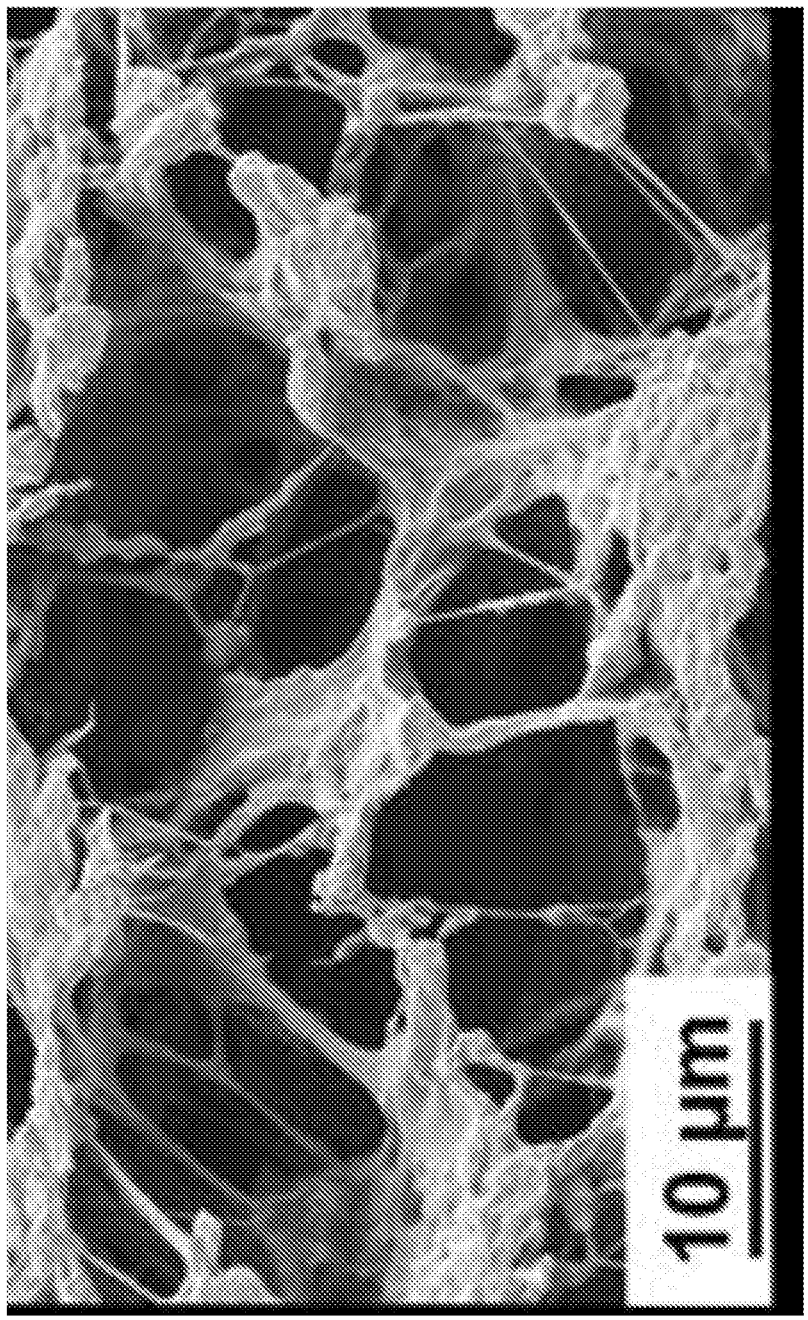

Scanning electron micrographs of cross-sections and surfaces of single 3D-printed fibers of 0, 25, 50, and 70% CuSO$_4$, comprising larger 3D-printed objects are displayed in FIG. 2B. This series of micrographs shows that as CuSO$_4$ content increased, the interior and exterior microstructure of the 3D-printed material increasingly became dominated by the CuSO$_4$ particles, and it became increasingly difficult to visually distinguish polymer from salt. In all instances, however, the exterior surface of the material appeared to be dominated by a thin layer of PLGA, where the layer became less defined in the 70% CuSO$_4$ composition. FIG. 2C shows an SEM image of a cut, salt-leached fiber of 70% CuSO$_4$, showing its unique porous structure.

It may at first seem counterintuitive that the higher the initial salt concentration within the material, the faster and more complete the salt leaching. However, the mechanism by which CuSO$_4$ and its constituent ions are removed from the 3D-printed material is based on diffusion—water must diffuse into the material to dissolve and dissociate the CuSO$_4$ particles/crystals (FIG. 2), and hydrated CuSO$_4$ ionic species must subsequently diffuse out of the material. The primary barriers to diffusion in this system were the PLGA walls. As the total, as-printed CuSO$_4$ content of the material decreased, the relative amount and volume of PLGA increased. This increase in PLGA content inhibited the capacity for water to diffuse into the interior of the material, and hydrated ionic species to diffuse out, resulting in higher residual salt content in samples with higher ratios of PLGA to CuSO$_4$.

Surprisingly, the order of the washing process (ethanol first, or water first) was found to not only substantially affect the rate of CuSO$_4$ dissolution, but also the final size of the resulting F-PLGA objects. For two, 1 cm diameter 70% CuSO$_4$ samples submerged in a large volume of water, the sample that had previously been washed in 70% ethanol was observed to leach faster than its counterpart not washed in ethanol. FIG. 3A clearly illustrates the change in size of 3D-printed 25, 50, and 70% CuSO$_4$ and resulting F-PLGA sheets as a result of being first washed in 70% ethanol, which is further quantified in FIG. 3C. 0, 25, 50, and 70% CuSO$_4$ objects washed first in 70% ethanol underwent an average linear dimensional expansion of 0, 2.3, 10.4, and 17.3%, respectively. While corresponding samples washed first in water underwent an average linear dimensional reduction of 0, 1.0, 3.1, and 5.0%, respectively. This volumetric change was independent of total mass loss, as illustrated in FIG. 3D. There is no statistical difference with respect to total mass loss between the two wash groups for any of the compositions.

Urrèloa et al. empirically measured and developed numerical models for the solubility of divalent salts, including CuSO$_4$, in ethanol-water. (See, S, Urrèloa et al., Journal of Chemical & Engineering Data 2011, 56, 2687.) They determined that CuSO$_4$ solubility, or saturation molality (m), decreases logarithmically with increasing ethanol weight fraction. Extrapolating their results to ethanol-water solutions comprised of 70% ethanol, the solubility of CuSO$_4$ is predicted to be less than 0.001 m/(mol·kg$^{-1}$) or, effectively non-soluble. This corresponds with the observation that the 70% ethanol wash, as a first step, did not substantially solubilize the CuSO$_4$ salt into the surrounding medium, which would have been observable as a color change. Thus, the CuSO$_4$ likely remained within the 3D-printed structure. Although it did not solubilize into the surrounding liquid medium, the 3D-printed constructs first washed in 70% ethanol was transformed from being off-white to bright blue in color, indicating that the CuSO$_4$ salt was interacting with the 30% water component of the solution and becoming hydrated to form CuSO$_4$5H$_2$O, copper sulfate pentahydrate.

This hydration resulted in a density decrease, or salt volume increase, of approximately 36% ($\rho_{CuSO_4}$=3.6 g/cm$^3$, $\rho_{CuSO_4 \cdot 5H_2O}$=2.3 g/cm$^3$). If the CuSO$_4$ volume fraction (including inherent porosity as shown in FIG. 4C) of each of the three 25, 50, and 70% CuSO$_4$ materials were increased by 36%, then the 3D-printed materials would be expected to undergo corresponding 8, 14.5, and 17.5% expansion, respectively. For the 70% CuSO$_4$, the predicted 17.5% expansion was near the empirically measured average value of 17.3%. However, as the CuSO$_4$ content decreased, the difference between the measured and predicted expansion increased. Without intending to be bound to any theory of the inventions, it is believed that the reason for this discrepancy is that as the CuSO$_4$ content decreased, the wall thickness of the PLGA matrix comprising the material increased (FIG. 4B), which resulted in a relative, local increase in matrix stiffness, while simultaneously providing a counter force that inhibited volumetric expansion of the PLGA matrix as a result of CuSO$_4$ hydration. The nature of the counter, contractile force of the PLGA matrix was indirectly evident from the linear dimensional reduction observed in samples first washed in water (FIG. 3C). In the instance of the samples first washed in water, the rapid dissolution of CuSO$_4$ into the surrounding medium permitted the surrounding, elastic PLGA matrix to contract slightly, resulting in a linear dimensional reduction of 1.0, 3.1, and 5.0% in the 25, 50, and 70% CuSO$_4$ 3D-printed materials, respectively. Ultimately, these results indicate that the composition of the washing and leaching solutions can impact the microstructure of the final material, and can even be utilized to increase the volume, as well as the porosity, of the 3D-printed object.

Figures 4A, 4B:
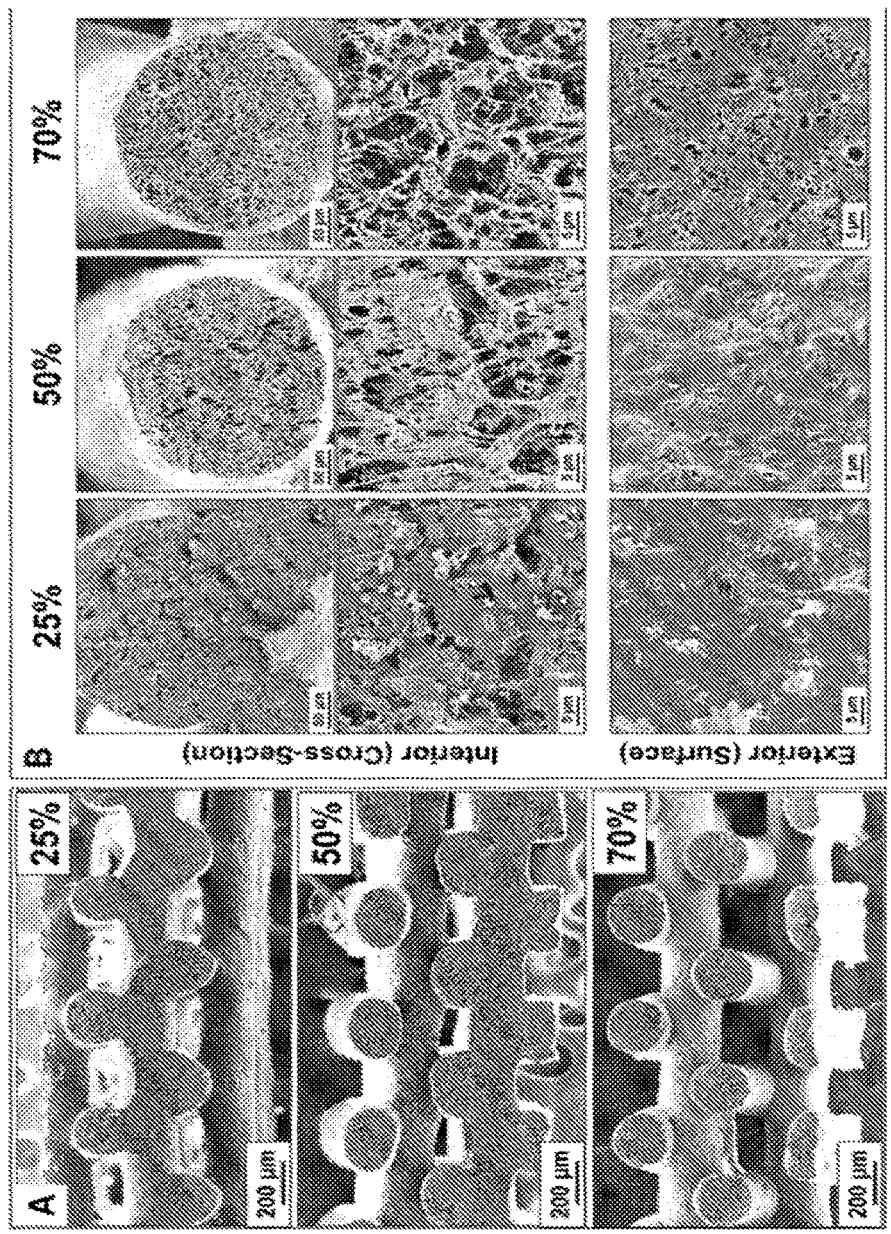
FIGS. 4A-4D. A) Representative scanning electron micrographs of cross-sections of 3D-printed 25, 50, and 70% F-PLGA (ethanol wash first). Note that structures in A) were 3D-printed in the 90°-Offset design; the same design utilized for the in vitro studies. B) Scanning electron micrographs of the interior cross-sections (low magnification and high magnification) and exterior surfaces of 25, 50, and 70% F-PLGA (ethanol wash first) 3D-printed fibers. C) Measured material porosity of as-printed and leached and washed (ethanol wash first) 25, 50, and 70% fibers. D) Average, relative absorbency of 25, 50, and 70% F-PLGA 3D-printed materials having been washed first in 70% ethanol followed by water (EthanolFirst) or first washed in $H_2O$ followed by 70% ethanol (Water First). Error bars denote standard deviation from average. * in C) and D): $p \leq 0.05$ for same compositional group under different wash conditions.
Figure 4C:
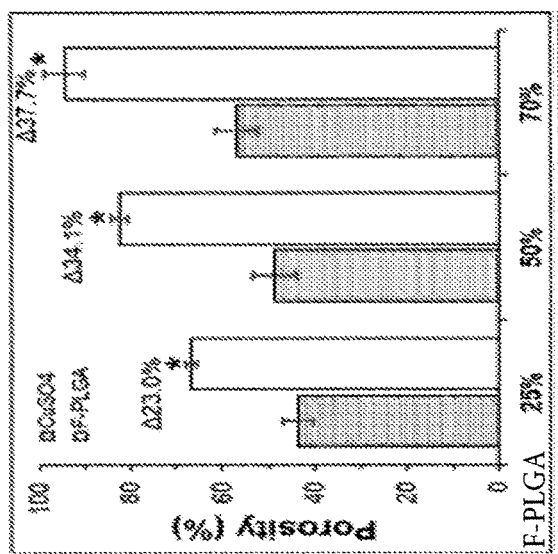

Scanning electron micrographs of washed (ethanol first) and lyophilized F-PLGA (FIGS. 4A and 4B) demonstrate that the overall 3D-printed structures of all material groups were preserved (FIG. 4A). Higher magnification micrographs of the F-PLGA cross-sections further validate the previously observed and quantified results (FIGS. 3A and 3B) that 25% F-PLGA did retain a significant amount of CuSO$_4$. CuSO$_4$ crystals (bright white) could be observed within the interior cross-sections and surfaces of 25% F-PLGA materials. Upon visual examination, there was no obvious presence of $CuSO_4$ crystals in either the 50% or 70% F-PLGA materials. These micrographs further validate that as the original $CuSO_4$ content was increased, the total porosity in the F-PLGA counterpart was also increased. Additionally, the average PLGA wall thickness defining the F-PLGA interior decreased with increasing $CuSO_4$ content, likely enhancing $CuSO_4$ leaching as described previously. Interestingly, the random, porous nature of the interior microstructure of the 70% F-PLGA resembled the microstructure of tissue- and organ-derived decellularized extracellular matrices—thin, fibrous walls (≤1 μm thick) surrounding pores 1-10 μm in diameter. The thin PLGA exterior layer observed in the as-printed $CuSO_4$ samples (FIG. 2) appeared to remain intact and relatively non-porous across the 25, 50, and 70% F-PLGA sample groups; however, micro- and sub-micro-scale surface porosity was observed within the 70% F-PLGA.

Porosity is exceptionally important for the biological application of materials, as it not only permits cells and tissues to interact and integrate with the material, but permits the material to uptake surrounding liquid and media (in vitro or in vivo), further enhancing integration, vascularization, and biofunctionality. Interestingly, in their as-printed $CuSO_4$ form, the inherent porosity between the 25, 50, and 70% groups was not significantly different (FIG. 4C) and resided between approximately 42% and 55%. Once washed and leached, however, the difference in porosity between F-PLGA groups became significant, with the 25% F-PLGA exhibiting the least porosity increase (43.6% to 66.6%; Δ23.0%), and 70% F-PLGA exhibiting the most (56.7% to 94.4%; Δ37.7%). With an average porosity of 94.4±4.3%, 3D-printed 70% F-PLGA was exceptionally porous.

Figure 4D:
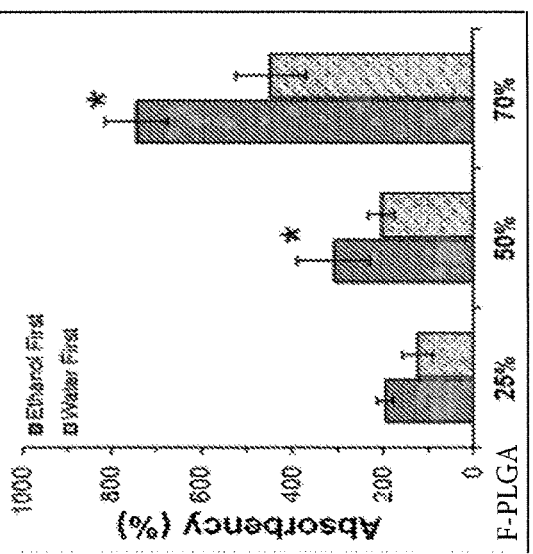

This high porosity translates directly to high absorbency, or the ability to retain liquid (aqueous-based, in this case). Whereas 25% F-PLGA structures having undergone ethanol followed by water washes can absorb an average of 195.6% their own solid weight in liquid water, 70% F-PLGA can absorb an average of 742.2% (FIG. 4D). The absorbency of 50% and 70% F-PLGA materials washed in ethanol followed by water is significantly higher than the absorbency of the same 3D-printed materials washed first in water followed by ethanol. Based on the large dimensional expansion of the material as a result of first being washed in ethanol, described earlier (FIG. 3), this is not surprising. Those materials washed in ethanol first are more voluminous, and are thus able to retain more liquid per unit material mass.

Mechanical Properties

Figure 5A:
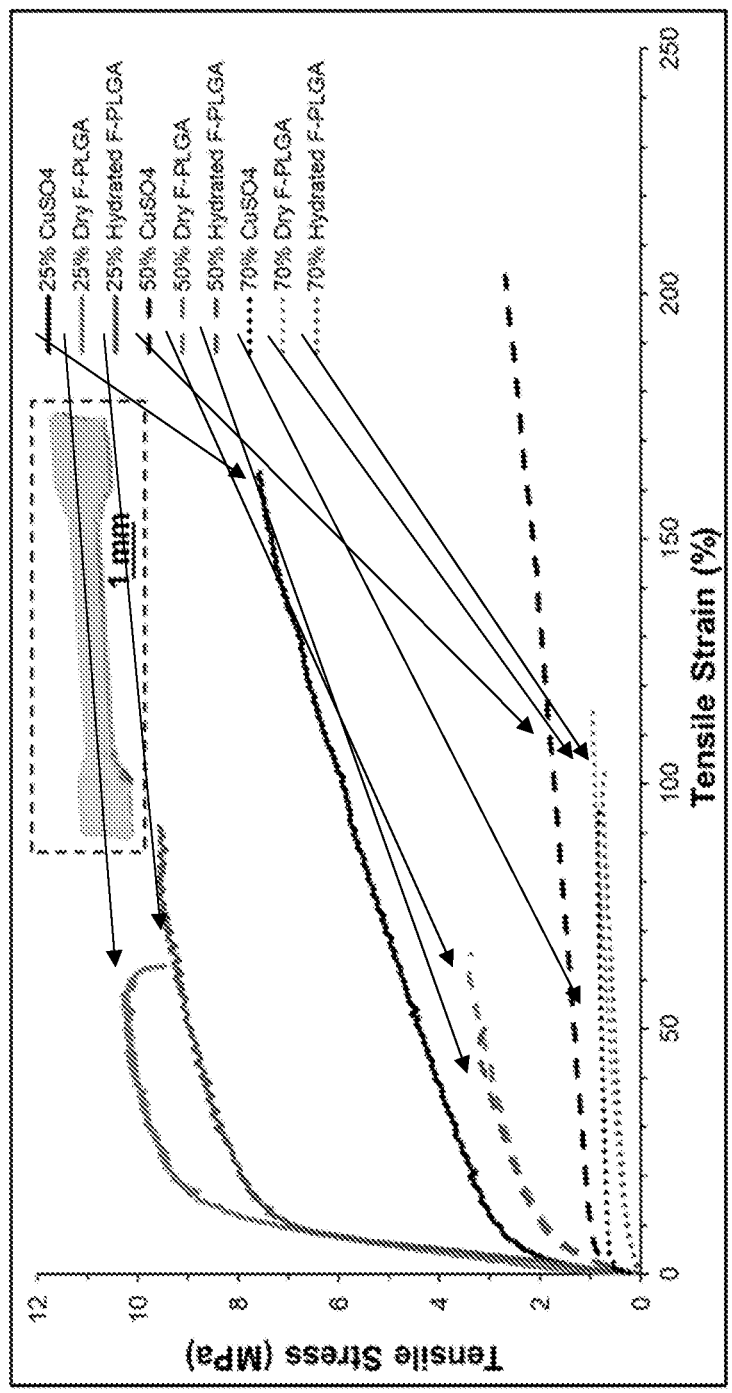
FIGS. 5A-5C. A) Representative tensile stress v. strain curves for 25, 50, and 70% as-printed samples ($CuSO_4$), samples that had been leached/washed and lyophilized (Dried), and samples that had been leached/washed, lyophilized and rehydrated. Inset shows an image of a typical 3D-printed tensile specimen (20 mm gauge length) utilized for the mechanical characterization. B) Average tensile moduli and C) percent strain to failure for each compositional group under as-printed, dry, and hydrated conditions. Error bars denote standard deviation from average. * in B) and C): $p \leq 0.05$ among compositional groups with the same treatment condition.

Like their microstructural and physical properties, the mechanical properties of the 3D-printed $CuSO_4$ and their F-PLGA counterparts vary substantially based on composition. FIG. 5A shows the representative tensile stress v. strain profiles of 25, 50, and 70% $CuSO_4$ and the F-PLGA counterparts in both dried (washed and lyophilized) and hydrated (washed, lyophilized, and rehydrated) conditions. Tensile specimens, such as those shown in the FIG. 5A detail, were 3D-printed directly. Comprehensive compression testing was not performed on these materials, primarily because the resulting data and analyses would be highly dependent on the particular 3D-printed geometry and not the material itself. However, desired compression testing can be performed on cylinders of material punched from larger 3D-printed blocks.

Figures 5B, 5C:
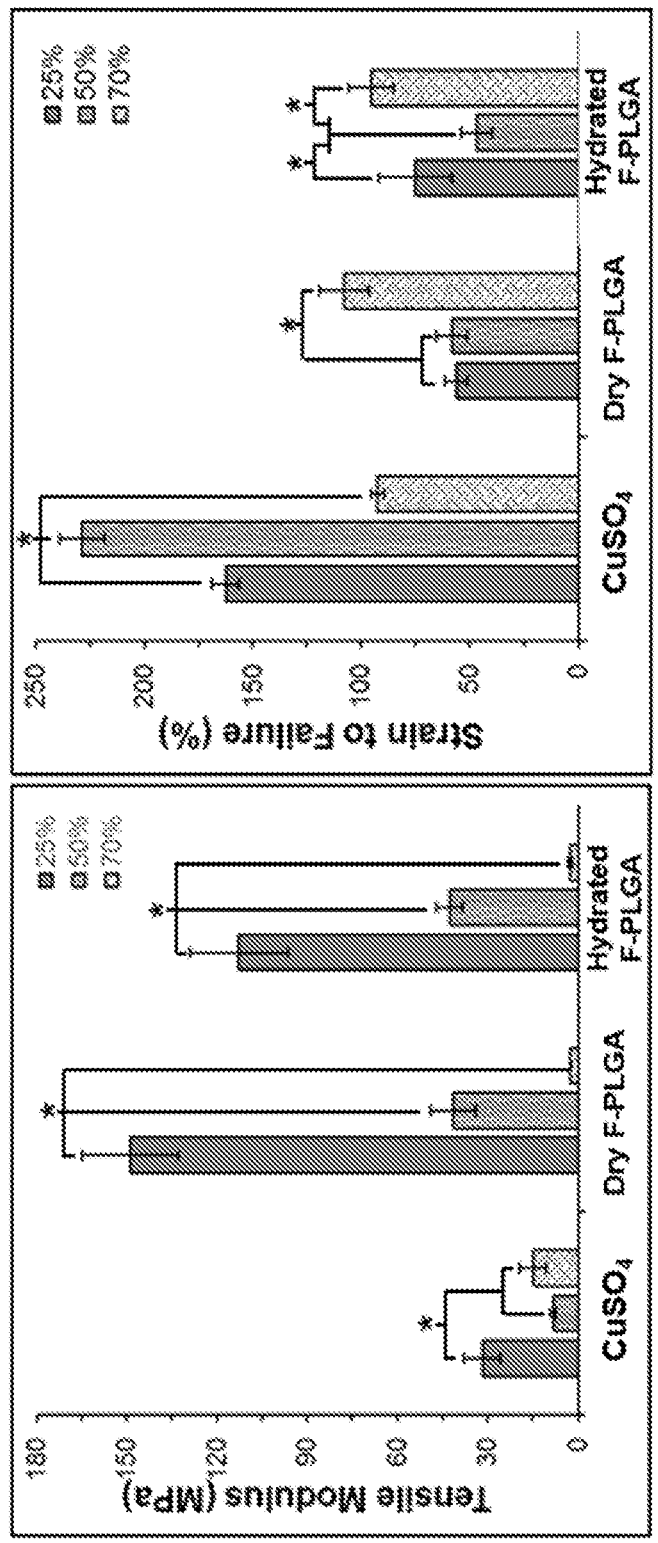

Notably, the hydrated condition most closely represents the end-use state—an aqueously saturated in vitro or in vivo environment. The tensile moduli tensile strains to failure are given in FIGS. 5B and 5C and are summarized, along with previously and discussed physical properties, in Table 1. In general, the lower the $CuSO_4$ content (higher PLGA content), the higher the ultimate tensile strength and tensile modulus of the material. Where ultimate tensile strengths in the hydrated state ranged from 9.5 MPa to 0.8 MPa for 25% and 70% F-PLGA, respectively, the elastic moduli ranged under the same conditions range from 112.6 MPa to 2.7 MPa for 25% and 70% F-PLGA, respectively. For purposes of biological comparison, these moduli ranged between that of auricular cartilage and pre-calcified bone. The strain to failure characteristics of the three material groups do not follow a clear trend, with the value in the hydrated state decreasing from 75.1% to 46.8% for the 25% and 50% F-PLGA, respectively, while the 70% F-PLGA in the hydrated conditions could undergo 95.2% tensile strain on average prior to failure. In aggregate, through this process, ultimate strengths ranging from 0.8-9.5 MPa, elastic moduli from 2.7 to 112.6 MPa, and strain to failure of 46.8 to 95.2% were demonstrated for the hydrated state.

Additionally, the three compositions tested demonstrate a strong, empirical, linear relationship between salt content and elastic modulus. To examine the capacity for this linear relationship to predict the composition required to produce an F-PLGA with the desired elastic moduli, 15 and 87 MPa were randomly selected as target moduli, and the corresponding, calculated $CuSO_4$ formulations (63.6% and 34.6% $CuSO_4$, respectively) were created, 3D-printed, washed, leached, lyophilized, and mechanically tested under tension. The results yielded F-PLGA materials with elastic moduli of 13.6±2.3 and 83.9±6.6 MPa, indicating that this simple linear extrapolation can be utilized to create F-PLGA with targeted moduli.

The mechanical properties of biomaterials significantly influence their overall in vitro and in vivo efficacy. Although the impact of biomaterials' mechanical properties with regard to cell and tissue interaction and integration is paramount with respect to both efficacy and safety, so too are biomaterials' mechanical and handling properties with regard to surgical use and effective and efficient clinical implementation. Thus, it is insufficient for a biomaterial intended for clinical translation to have biologically safe compositions and elevated porosity. The biomaterial must also have the appropriate mechanical properties that not only promote a positive cellular and tissue response, but also permit them to be effectively utilized within a clinical setting. When the hydrated, 70% F-PLGA was handed to a trained, clinical plastic surgeon without a description of what the material was, the surgeon noted that it felt and behaved very similar to ear or nose cartilage.

TABLE 1

Summary of the physical and mechanical properties of 25, 50, and 70% 3D-printed F-PLGA (ethanol wash first) under dry and hydrated (Bold) conditions. Note that Porosity and Absorbency are only given for hydrated conditions due to the requirement for measurement and subject of measurement.

|  | 25% | 50% | 70% |
|---|---|---|---|
| Porosity [%] | 66.6 ± 1.1 | 82.5 ± 1.9 | 94.4 ± 4.3 |
| E [MPa] | 148.9 ± 16.1 | 41.3 ± 7.5 | 2.4 ± 0.3 |
|  | 112.6 ± 16.4 | 42.6 ± 4.4 | 2.7 ± 0.8 |
| UTS [MPa] | 10.2 ± 1.6 | 3.4 ± 0.6 | 1.0 ± 0.1 |
|  | 9.5 ± 1.1 | 3.2 ± 0.8 | 0.8 ± 0.2 |
| F % | 56.2 ± 5.3 | 58.1 ± 7.0 | 107.8 ± 11.4 |
|  | 75.1 ± 17.0 | 46.8 ± 7.2 | 95.2 ± 10.4 |
| Absorb. [%] | 195.7 ± 18.7 | 310.0 ± 79.7 | 742.2 ± 69.7 |

Human Mesenchymal Stem Cells Attachment, Viability, and Proliferation

Figure 6B:
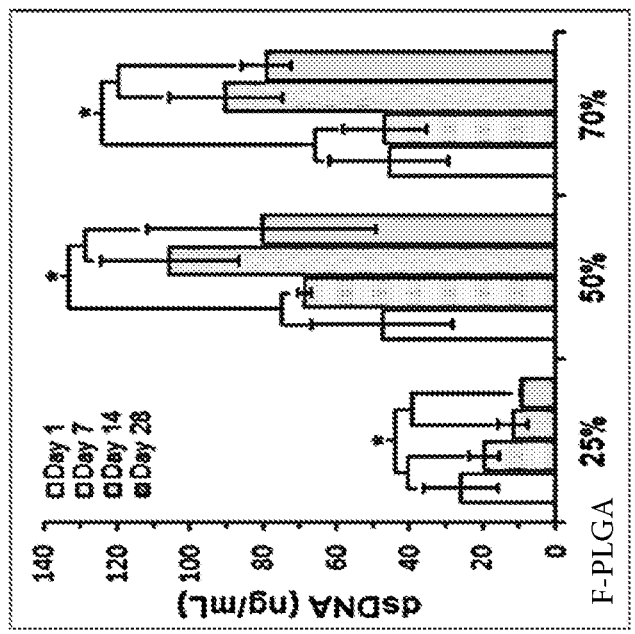
FIGS. 6A-6B. A) Top-down views of live-dead scanning fluorescent confocal three-dimensional reconstructions of hMSCs on 0, 25, 50, and 70% F-PLGA 1, 7, 14, and 28 days after initial cell seeding. 0% images are from previously published work by Jakus et al. (See, A. E. Jakus, et al., Acs Nano 2015, 9, 4636.) B) Average quantities of double stranded DNA (dsDNA) found within each material group at 1, 7, 14, and 28 days after initial seeding.
Figure 6A:
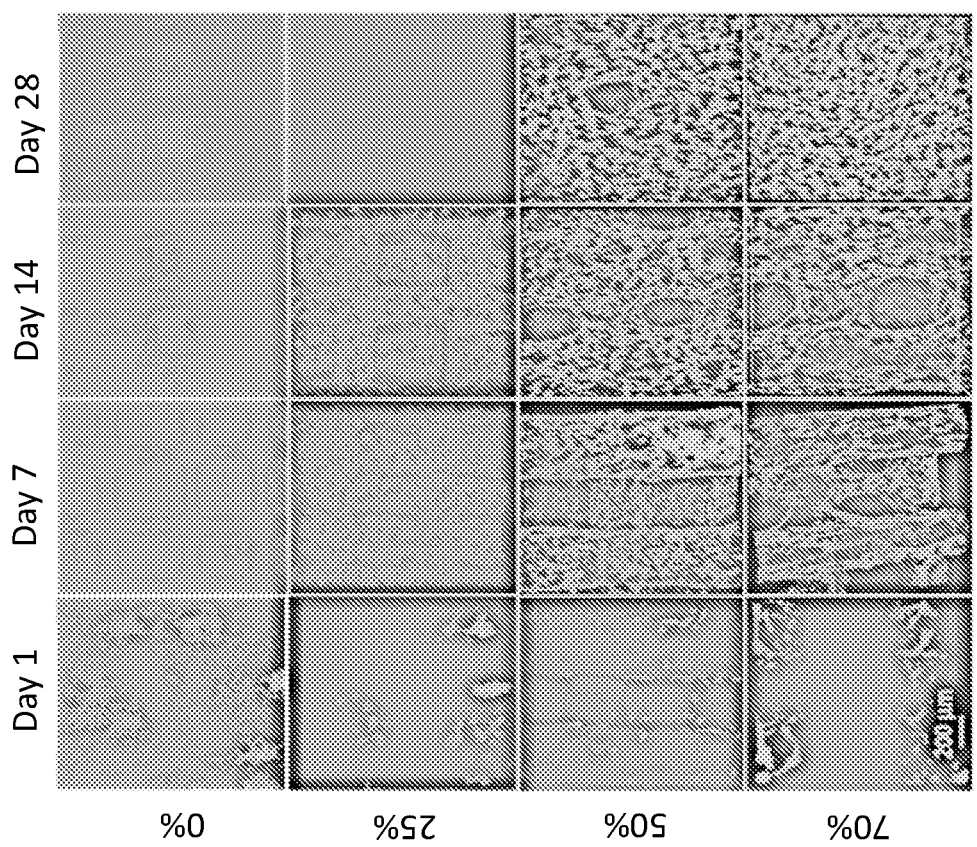

Ultimately, if a material is intended for biological applications, it must support cell adhesion, viability, proliferation, and matrix deposition. To this end, the cytocompatibility of 25, 50, and 70% F-PLGA (and compared them with a 0%, pure PLGA historical control) was tested by seeding female human mesenchymal stem cells (hMSCs) onto 3D-printed scaffolds of each material, and the cell viability and number after 1, 7, 14, and 28 days were examined. hMSCs were selected because they are a clinically relevant cell type, often used in clinical procedures after being isolated from patient bone marrow. To create the scaffolds for seeding, large 5×5 cm sheets, such as those shown in FIG. 3A, were 3D-printed with an alternating 0-90°, 0.7 mm (strut center-to-center distance) pattern, with every other strut offset 0.35 mm from the prior printed parallel layer. Cross-sections of this design are shown in FIG. 4A. At each time point, one sample from each group was visualized and examined for cell viability using live-dead cell staining and scanning laser confocal microscopy (FIG. 6A). Additionally, the average total double stranded DNA (dsDNA) content for each material group was quantified at each time point (FIG. 6B), where the dsDNA content directly corresponds with cell number, and can indicate if the cells are increasing or decreasing in number relative to neighboring time points.

It was clear from both the live-dead imaging results as well as the dsDNA quantification that 25% F-PLGA, like 0% historical control, did not support hMSC viability or proliferation. At day 1, there were a minimal number of viable hMSCs present, but as time went by this number further decreased. Conversely, both 50% and 70% F-PLGA supported hMSC adhesion and proliferation over time, with cell numbers peaking at day 14 and not significantly changing over the course of the next two weeks (FIG. 6B). This proliferation can clearly be seen in the live-dead images (FIG. 6A), as can the high cell density in the day 14 samples, appearing to nearly fill the scaffold volume, likely preventing further proliferation by day 28.

Figure 7:
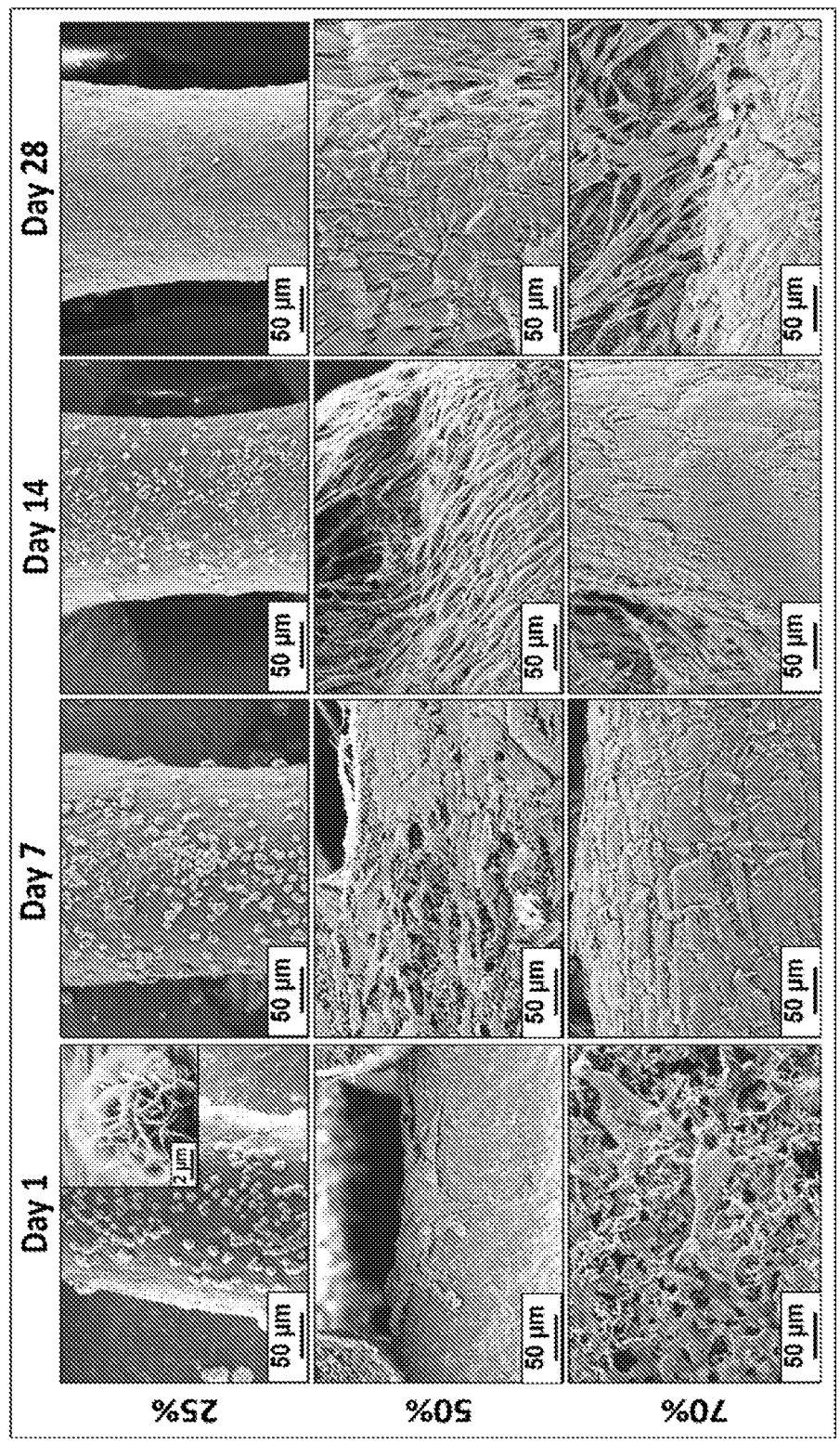
FIG. 7. Representative scanning electron micrographs of hMSCs on 25, 50, and 70% F-PLGA 1, 7, 14, and 28 days after seeding.

Scanning electron micrographs (FIG. 7) further elucidate the interactions of the hMSCs with the underlying F-PLGA materials. The conclusions drawn here are based on these micrographs, as well as the prior material characterization results (FIGS. 3A and 3B and FIG. 4B). In stark contrast, hMSCs could be seen spreading and completely coating the 50% and 70% F-PLGA scaffolds over the course of the 4 weeks, forming thick, yet viable, cellular murals. Some cells were even observed extending into the porous framework of the 70% F-PLGA.

These results tentatively indicate that 25% F-PLGA is not an optimal biomaterial, because hMSCs did not positively interact with it. Upon initial examination of the data and results from this work, the reason for this lack of cell-adhesion would at first seem to be the presence of significant amounts of $CuSO_4$ in the material (FIG. 3B). However, the hMSC in vitro culture results for 25% F-PLGA were very similar to the historical control, 0%, which never contained or came into contact with $CuSO_4$ at any point during the fabrication process, but had little to no porosity and a very smooth surface (FIG. 2B). Based on these combined observations, the reason the hMSCs did not adhere to 25% F-PLGA was either because they contained too much residual $CuSO_4$ (390.2 µg/dL; FIG. 3B), they were not porous enough (FIG. 4B), or a combination of these factors. Thus, it is clear that porosity and by extension, material processing plays a major role in the success of the F-PLGA. These results highlight the importance of processing and porosity in biomaterials, as the 0 and 25% F-PLGA materials had the exact same final composition (purely PLGA) as the 50 and 70% F-PLGA materials; yet, the 50 and 70% F-PLGA performed substantially better, promoting stem cell adhesion, proliferation, and function.

F-PLGA as a Physical Scaffold for Weak Hydrogels

It has thus far been demonstrated that a materials-centric 3D-painting process can be utilized, combined with a salt leaching approach, to create 3D-printed, highly porous, medical grade PLGA structures with excellent physical, mechanical, and biological characteristics. However, regardless of how well the 50% F-PLGA or 70% F-PLGA materials and scaffolds perform in vitro with stem cells, they are still a purely synthetic, non-functionalized, non-tissue specific, polyester. However, because the F-PLGA materials are highly absorbent, mechanically robust, and surgically friendly in terms of handling, they can serve as a physical scaffold for materials with high, tissue-specific bioactivity, but poor mechanical and handling properties, such as liquid solutions and gels. These materials include solutions and gels laden with growth factors, drugs, and cells where the gels can be composed of natural, synthetic, or hybrid materials such as gelatin, collagen or atelocollagen, extracellular matrices, alginate, chitosan, or peptide amphiphiles, among many others.

Figure 8:
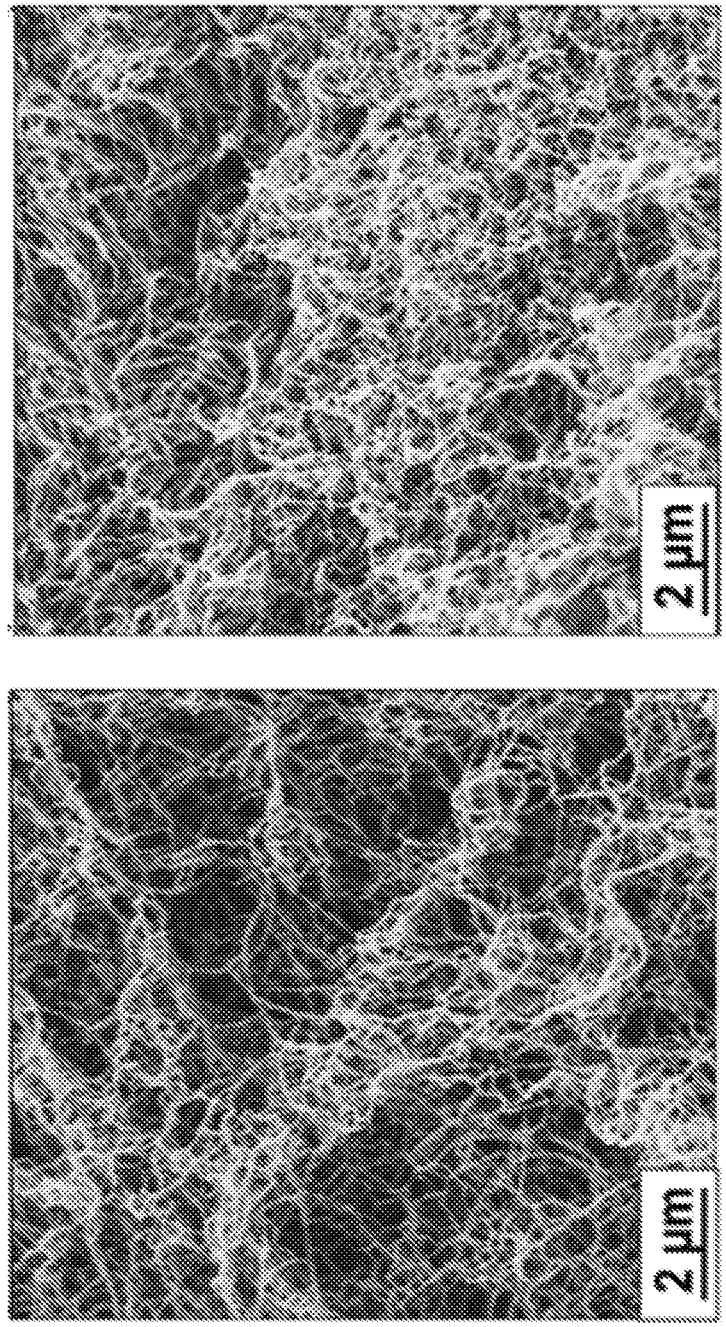
FIG. 8. Scanning electron micrographs (SEM) of the interior of 70% F-PLGA scaffolds infused with atelocollagen or peptide amphiphile solutions that were subsequently gelled.

To briefly demonstrate the potential for F-PLGA to act as a scaffold or carrier for mechanically weak, difficult to localize materials, two distinct types of weak gels were created: 0.25% atelocollagan (naturally derived) and 0.25% peptide amphiphile (PA). These types of low solids content gels can be beneficial due to their ability to be injected, but are difficult to localize in vivo and migrate over extended periods of time, often requiring secondary tissue flap closures. This ultimately inhibits their effectiveness and clinical translation. FIG. 8 shows the atelocollagen and PA gels being injected into a 1 cm diameter 70% F-PLGA scaffold cut from a much larger 3D-printed sheet. To ensure maximum saturation, the pre-gel solutions were injected until the scaffold began overflowing, at which point the appropriate gelation process (thermal for atelocollagen; divalent ion cross-linking for the PA) was utilized to gel the material within the scaffold. The gel-laden F-PLGA could be picked up with forceps and otherwise handled. Scanning electron microscopy revealed that the interiors of the F-PLGA scaffolds were laden with nano-fibular atelocollagen or peptide amphiphile networks. This very simple experiment demonstrated that materials such as F-PLGA, which is 95% porous, can act as carriers for biomaterials that are more liquid than solid in nature. Because the F-PLGA is a simple, biomedical polyester that contains no specific functionality, it is hypothesized that the bioactive gel would dominate the biological response once implanted, while the presence of the F-PLGA would allow a surgeon to: 1) handle and implant the gel; and 2) localize and retain the gel at the target location, mitigating near and long-term migration.

Because the F-PLGA is almost entirely porous, has mechanical properties that more closely match those in the body, is able to retain large volumes of liquid, and is made completely of base medical grade material that is already frequently, clinically utilized and recognized, the approach described herein is well-suited to hold gels and cells.

Extending the Approach to Create Porous 3D-Printed Graphene, Metal, and Ceramic Materials Finally, it is possible to extend this pore forming approach described in this example to other material systems, pushing the applications of this approach beyond medicine and tissue engineering. To demonstrate that this approach can be applied to introduce porosity into a variety of material systems, composite compositions were created of $CuSO_4$ and the following: nickel (Ni) metal, yttria stabilized zirconia (YSZ) ceramic, and graphene (Gr), which are representative of metal, ionic, and covalent solid systems. Each compound composition was comprised of 30 vol. % PLGA, 35 vol. % $CuSO_4$, and 35 vol. % Ni, YSZ, or Gr. These compositions were ultimately used to produce F-Ni, F-YSZ, or F-Gr (after washing).

Squares of each material were 3D-printed via direct, room-temperature extrusion, the same as the $CuSO_4$ compositions, from which 6 mm diameter samples were punched (FIG. 9A). These samples underwent the same wash and lyophlization procedures as the $CuSO_4$ only samples; the residual copper ion content quantification is shown in FIG. 9B (analogous to 3B for F-PLGA). Because the ultimate use applications of the YSZ ceramic and Ni metal would be in sintered states, the F-YSZ and F-Ni were sintered (F-YSZ in air, F-Ni in hydrogen gas) after washing. Scanning electron micrographs of the interior microstructures of 3D-printed F-Gr, F-Ni, and F-YSZ at all processing states are shown in FIG. 9C. F-YSZ, like 70% F-PLGA, is almost completely free from residual copper ions, while F-Gr and F-Ni are not (FIG. 9B). It is believed that, due the very high surface area of graphene, it is likely that dissociated copper ions became adsorbed to graphene flakes within F-Gr, preventing them from being leached into the surrounding media. In the case of the F-Ni, $CuSO_4$ in solution has been known to spontaneously react with and substitute for Ni metal (complete solid-solid solubility of Cu and Ni). This high affinity of Cu for Ni likely mitigates the complete removal of copper ions during washing. Indeed, salt crystals can be seen in the micrographs of the washed F-Gr and F-Ni samples (FIG. 9C; bright crystals).

Figure 9E:
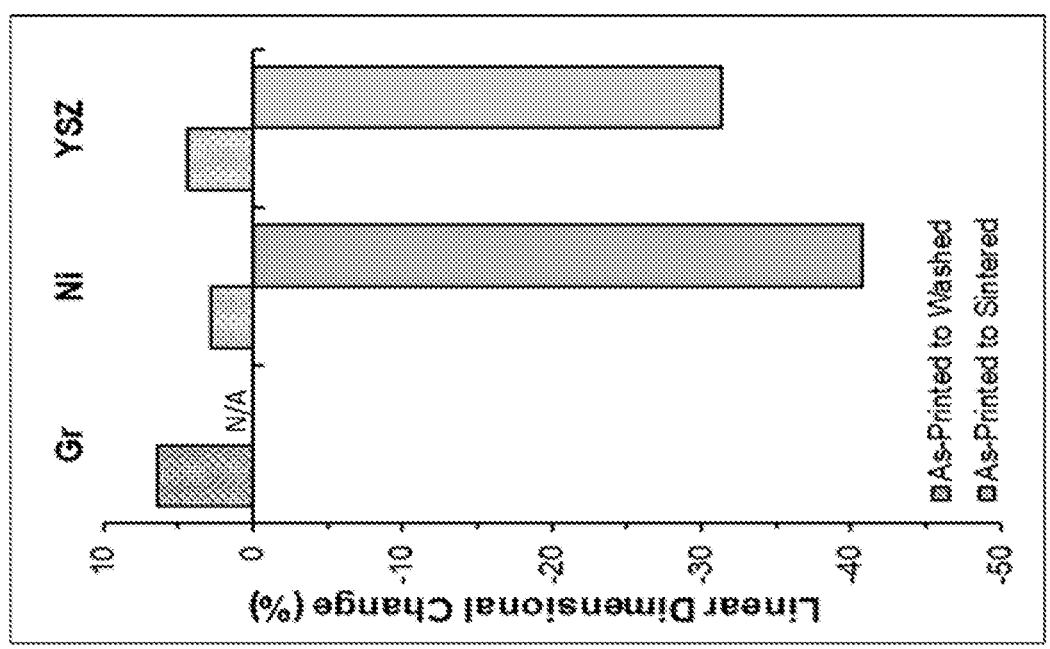

Like the original $CuSO_4$ 3D-printed materials, ethanol washing followed by water washing results in a slight linear dimensional increase (FIG. 9E) for all materials (2-6%). This size increase is slightly less than that of the of 50% $CuSO_4$ to F-PLGA, which is consistent with prior observations, as the previous system had 50 vol. % $CuSO_4$ solids, and the current F-Gr, F-Ni, and F-YSZ materials have 35 vol. % $CuSO_4$ solids. Despite the high porosity, the F-Ni and F-YSZ could be effectively sintered in hydrogen and air atmospheres, respectively. Because of the elevated porosity, the final size of the sintered materials were dramatically smaller than their original as-printed or as-washed forms. This obvious change in size is shown dramatically in FIG. 9D for the F-Ni, where the final object was 40% smaller in all directions relative to its as-printed counterpart, and retained substantial internal porosity (FIG. 9C). Similarly, F-YSZ underwent a substantial dimensional reduction (30%) as a result of sintering, but maintained microstructural porosity (FIG. 9C). To demonstrate the transformation that occurred between the as-3D-printed $CuSO_4$+YSZ and the resulting sintered F-YSZ, samples of each state were exposed to a high temperature blow torch. As expected, the non-sintered sample burned and fell apart, while the sintered YSZ maintained its shape. The F-Gr, F-Ni, and F-YSZ shown here represent the ability to add porosity into a wide variety of 3D-printed material systems for an extensive range of applications.

Materials and Methods:
3D-Printing Composition Synthesis $CuSO_4$ compositions were synthesized based on previously established methods. (See, A. E. Jakus, S. L. Taylor, N. R. Geisendorfer, D. C. Dunand, R. N. Shah, Advanced Functional Materials 2015, 25, 6985.) Briefly, the appropriate amount of PLGA (82:18 lactide:glycolide; density=1.15 g/cm$^3$) copolymer (Evonik Cyro, USA), depending on the composition ratio to be made, was fully dissolved in dichloromethane (DCM; Macron Fine Chemicals, USA; 10 mL DCM per gram PLGA). Separately, a mixture of DCM, 2-butoxyethanol (2-Bu; Sigma Aldrich, USA), and dibutyl phthalate (DBP; Sigma Aldrich, USA) in a ratio of 20:2:1 was prepared in which the appropriate volume of $CuSO_4$ (Alfa Aesar, USA; density=3.6 g/cm$^3$), which had been previously sieved to obtain −325 mesh powder, was suspended and mixed for several minutes. 0.9 g 2-Bu and 0.45 g DBP were utilized for every 3.6 g of $CuSO_4$ used to create the composition (corresponding to approximately 9 g DCM per 3.6 g $CuSO_4$ used). The dissolved PLGA and $CuSO_4$ powder suspensions were then physically combined and mixed via manual stirring for several minutes until the mixture appeared homogenous. The resulting pre-composition was allowed to thicken in a chemical fume hood via ambient condition DCM evaporation over the course of several hours, in conjunction with regular stirring, until the appropriate, low-shear viscosity of 30 to 35 Pa·s had been reached. This viscosity value was ideal for 3D-printing and measured using a couette fixture with a solvent trap (MCR Rheometer, Paar Physica) under rotational shear at interval stresses between 0 and 100 Pa. This process was utilized for all $CuSO_4$ compositions used in this work (25, 50, and 70% by solids volume, and 63.6 and 35.6% $CuSO_4$ compositions), as well as the mixed $CuSO_4$+Graphene, $CuSO_4$+Ni metal, and $CuSO_4$+YSZ mixed compositions. The solids volume contents of the mixed compositions were 30% PLGA, 35% $CuSO_4$, and 35% graphene powder (Graphene Labs, USA; 5-25 µm lateral dimensions), nickel metal powder (Alfa Aesar, USA; 3-7 µm), or YSZ (Fuel Cell Materials Inc., USA; 0.9-1.2 µm). Pure PLGA compositions were not fabricated for this work, but were previously fabricated, 3D-printed, and characterized as described by Jakus et al. (See, A. E. Jakus, et al., ACS Nano 2015, 9, 4636.) Final $CuSO_4$ and compound compositions were either 3D-printed immediately or stored in sealed glass jars at 4° C. until needed.

3D-Printing

All printed structures were fabricated using a 3D-Bioplotter (EnvisionTEC GmbH, Germany) via room-temperature pneumatic syringe extrusion. $CuSO_4$ compositions were poured into 30 cc cartridges (Nordson EFD, USA) and loaded onto the 3D-Bioplotter. Conical plastic or stainless steel 250 µm diameter nozzles (Nordson EFD, USA) were used to create the majority of samples utilized throughout this work. 410, 500, and 600 µm nozzles were utilized for additional, non-quantifiably characterized samples. 5-layer (200 µm/layer) 5×5 cm squares were 3D-printed from each of the 25, 50, and 70% $CuSO_4$ compositions using the 250 µm nozzles and linear print speeds of 20-40 mm/s. The previously described 0-90° offset design was utilized as the internal print pattern for each of these sheets. (See, A. E. Jakus, et al., Science translational medicine 2016, 8, 358ra127; A. E. Jakus, et al., ACS Nano 2015, 9, 4636; and A. E. Jakus, et al., Journal of Biomedical Materials Research Part A 2017, 105A.) Briefly, parallel fibers within a single layer were extruded 0.8 mm apart (center fiber to center fiber distance), resulting in a 200-300 µm distance between fibers within a given layer. The next layer was printed in the same way, but orthogonal to the first. Every other layer was printed at a 400 µm offset in the X-Y plane relative to the previously printed parallel layer. This ultimately resulted in a staggered, alternating 0-90° pattern that was ideal for cell seeding and in vitro studies.

Washing/Leaching and Lyophilization 3D-printed $CuSO_4$ 5×5 cm sheets, as well as tensile "dog bone" specimens were washed and leached by submerging individual specimens in 200-300 mL 70% ethanol in 500 mL beakers. The beakers were placed on magnetic stir plates and stirred at low speeds to ensure continued movement of the samples. This was done for 1 hour, at which point the 70% ethanol was exchanged for fresh ethanol and the samples were washed an additional 30 minutes. In a sterile, tissue culture hood, the 70% ethanol was replaced with sterile water, covered with sterile foil, and washed on the magnetic stir plate for an additional 30 minutes. The resulting samples were then frozen for several hours at −80° C. and lyophilized for ~24 hours to yield dry samples. The $CuSO_4$+graphene, $CuSO_4$+Ni, and $CuSO_4$+YSZ were also washed, leached, and lyophilized according to this process. As described in this work, a variant of this process, with the water washing step before the ethanol step, was utilized for some samples to look at the impact of washing protocol on the materials.

Porosity

The porosity of as-printed $CuSO_4$ materials was determined according to previously described methods. (See, A. E. Jakus, et al., Science translational medicine 2016, 8, 358ra127; S. L. Taylor, A. E. Jakus, et al., Advanced Engineering Materials 2016, n/a; and A. E. Jakus, et al., Journal of Biomedical Materials Research Part A 2017, 105A.) Briefly, approximately 1 m fiber (250 µm nozzle extruded) of each $CuSO_4$ type was extruded, collected, and lyophilized (not washed). The fibers where then cut into sections of known length and massed. Based on the known compositions and dimensions of the fibers, along with their measured masses, their density was determined. This measured density was compared to the theoretical solid density (based on the ratio of $CuSO_4$ and PLGA within a given material if the fiber had no porosity), producing a porosity value. A similar process was utilized for washed and leached F-PLGA fibers, assuming that all $CuSO_4$ had been removed (a reasonable approximation based on the data).

Mechanical Testing 1 mm thick (5 layer), 20 mm gauge length "dog bone" specimens were 3D-printed from each material (described earlier). All mechanical testing was performed using an LF Plus mechanical tester (Lloyed Instruments, USA). All samples were measured at 2 mm/min tensile displacement speeds. As-printed CuSO4 samples were stored in sealed 50 mL centrifuge tubes prior to mechanical testing. Dry samples were evaluated immediately after being lyophilized. Additional lyophilized samples were submerged in water for 30 minutes prior to mechanical testing (hydrated). Three samples were tested for each composition and sample condition. The elastic modulus for each sample was determined based on a 2% strain offset linear slope from 0% strain. Compressive tests on 3D-printed 50% $CuSO_4$/F-PLGA samples were performed on 1 cm tall, 5 mm diameter cylinders punched from larger 1 $cm^3$ blocks (described earlier), as-printed, washed and lyophilized, and washed, lyophilized and hydrated.

hMSC Seeding and Culture

Passage 2 female human bone marrow derived mesenchymal stem cells (Lonza, Walkersville, MD USA) were expanded up to passage 5 using MSC basal medium and proliferation kit (Lonza) according to the manufacturer's instructions. 5 mm diameter scaffolds were punched from each of the 25, 50, and 70% F-PLGA 5×5×0.1 cm (initial print size; 5 layers, 0-90° offset as described previously) sheets (scaffold n=32 of each material; 8 for each of four timepoints timepoint). Scaffolds were sterilized in 70% ethanol for 1 hour, followed by three 5 minute washes in sterile water to remove ethanol. Scaffolds were placed into individual wells in 48-well plates. Prior to cell seeding, excess water was aspirated out of each scaffold. Each scaffold was statically seeded with 20,000 hMSCs suspended in 5 µL media (1×low glucose Dulbecco modified eagle medium modified with 10% fetal bone serum), HEPES buffer, 1-glutamine, and ten units antibiotic antimyotic (Invitrogen, USA). 200 µL of this medium was added to each well 45 minutes after initial seeding. All cell seeded samples were incubated at 37° C. in 5% $CO_2$. One sample from each material group was removed at designated time points (1, 7, 14, 28 days) for imaging (confocal and scanning electron microscopy), 4 for dsDNA quantification, and 3 to be frozen at −80° C. for future use if needed.

Live/Dead Imaging

Samples reserved for confocal fluorescence imaging were first rinsed in sterile phosphate buffered saline (PBS) and incubated in a PBS solution of $5\times10^{-3}$ m calcein AM and $5\times10^{-3}$ m ethidium bromide homodimer (Invitrogen, USA) for 30 min prior to imaging. A Nikon C2+ fluorescent scanning confocal microscope (Nikon, USA) was used to obtain a series of images through the top ~500 µm of each sample. Images were reconstructed into 3D representations using ImageJ software (NIH).

dsDNA Quantification

Specified samples at each of 1, 7, 14, and 28 day time points were prepared for DNA quantification measurements by first lysing cells via sonication for 45 min at room temperature in 1 mL of 0.02 wt. % triton-X 100 (Bio-Rad, USA) solution in DNA-free water, Lysates were stored at −80° C. until the quantification was performed. Double stranded DNA (dsDNA) within cell lysates was quantified via fluorescent assay using Quanti-iT™ PicogreenVR dsDNA Assay Kit (Invitrogen, USA), according to the manufacturer's instructions.

Scanning Electron Microscopy

Samples without cells were prepared for scanning electron microscopy (SEM; LEO Gemini 1525; 3 kV accelerating voltage) by coating with 15 nm osmium metal via osmium plasma (Osmium Coater, SPI Supplies) prior to imaging. Samples with cells from in vitro studies were prepared directly from samples imaged with Live/Dead staining and imaged using confocal microscopy. Immediately after confocal fluorescence imaging, samples were fixed in a solution of 3 wt. % sucrose (Sigma Aldrich, USA) and 2 wt. % glutaraldehyde (Sigma Aldrich, USA) in sterile nanofiltered water for 30 min followed by graded ethanol washes starting from 50% up to 100%, after which the samples were critically point dried (Critical Point Dryer, Tousimis Samdri, USA). Samples were then coated with 15 nm osmium prior to imaging (LEO Gemini 1525, USA). F-PLGA samples containing atelocollagen and peptide amphiphile gels were dehydrated using the graded ethanol wash, critically point dried, and coated with osmium as described above prior to imaging.

Example 2

In this example, the osteoregenerative capacity of "hyperelastic bone" (HB) is compared to a clinical standard, autologous bone in rat critical-sized calvarial defects. Although a porous, $CuSO_4$-leached F-PLGA scaffold is used as a control is this example, this example demonstrates that the porous, $CuSO_4$-leached F-PLGA scaffold rapidly integrate with host tissue, vascularize, can encourage tissue formation, and is generally safe for implantation. Moreover, it can be understood from this example, that a porous, $CuSO_4$-leached F-PLGA scaffold can be modified to include bioactive ceramic particles, such as hydroxyapatite, to enhance its tissue growth promoting properties.

Material and 3D-Printed Scaffold Preparation:

HB was synthesized and characterized as previously described using good medical practices (GMP)-grade hydroxyapatite (HA) (Merz North America) and PLGA (Evonik Cyro). (Jakus, et al., Sci Transl Med 2016; 8:358ra127.) F-PLGA was fabricated from copper sulfate (Alfa Aesar)/PLGA (Evonik Cyro) inks that had been 3D-printed and salt-leached. F-PLGA served as a 3D-printed, hydroxyapatite-free control. All samples were 3D-printed using a 3D-BioPlotter (EnvisionTEC, GmbH). 5×5-cm sheets of each material, five layers thick (120 µm per layer, for a total of 0.6 mm) with a progressive 120 pore pattern were produced using a 200-µm nozzle and 250-µm spacing between adjacent parallel fibers. Eight-mm diameter scaffolds for implantation were punched from the 5×5-cm sheets using a biopsy punch and washed and sterilized according to previously described protocols (Jakus, 2016).

Surgical Procedure:

Adult male Sprague Dawley rats weighing approximately 500-g each were obtained from Charles River Laboratories International, Inc. (Wilmington, MA). All animal surgical procedures were approved by and performed according to the guidelines established by the University of Illinois at Chicago Animal Care and Use Committee. Rats were maintained with general anesthesia (2% isoflurane/100% $O_2$) during the procedure. Under routine sterile conditions, the calvarium between the coronal and lambdoid sutures was exposed through a 1.5-cm sagittal incision. A handheld drill fitted with a trephine was used at low speed with sterile normal saline irrigation to create a full-thickness 8-mm diameter calvarial defect. (Spicer, P. P., Kretlow, J. D., Young, S., Jansen, J. A., Kasper, F. K., Mikos, A. G. Evaluation of bone regeneration using the rat critical size calvarial defect. Nat Protoc 2012; 7:1918-1929.) The defects were randomly allocated into the following study groups: (1) empty defect (negative control) (n=7); (2) defect implanted with autologous calvarial bone (positive control) (n=6); (3) defect implanted with F-PLGA scaffold (n=6); and (4) defect implanted with HB scaffold (n=10). Periosteum and skin was closed using a running absorbable suture and buprenorphine SR LAB (0.1 mg/kg) was administered subcutaneously for analgesia. Animals were housed 2 per cage with ad libitum access to water and food. Rats were sacrificed at 8 (n=16) and 12 weeks (n=13) postoperatively. The skull samples containing defect sites were retrieved and fixed in 10% neutral buffered formalin for analysis.

The results demonstrated that by using an HB scaffold that includes PLGA and HA microparticles within the scaffold, the osteoconductivity was increased to accelerate bone regeneration in critical-sized calvarial defects. When normalized to the clinical standard of autologous grafts, CBCT and micro-CT analysis of bone formation 8 and 12 weeks post-implantation showed a greater volume of new bone formation with the HB scaffolds. However new bone formation was also observed in the salt-leached PLGA HA-free scaffolds.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of forming a porous material system, the method comprising:
   using a viscous composition comprising a solids content to form a three-dimensional object, the viscous composition comprising a viscosity of 1 pascal second or more, and the solids content comprising:
      solid particles, at least some of which are water-soluble salt particles; and
      a polymer, the polymer acting as a binder for holding the solid particles together;
      wherein the solid particles are at least about 20 vol. % of the solids content;
   after the forming the three-dimensional object, hydrating the water-soluble salt particles by exposing the three-dimensional object to a salt-hydrating solution, wherein the water-soluble salt particles are hydratable salt particles that do not dissociate but undergo an increase in volume due to hydration in the salt-hydrating solution; and
   after the hydrating step, dissolving at least a portion of the hydrated, water-soluble salt particles in water, thereby forming the porous material system.

2. The method as in claim 1, wherein the using a viscous composition to form the three-dimensional object step is performed at room temperature.

3. The method as in claim 1, wherein the using a viscous composition to form the three-dimensional object step is performed at a temperature that is sufficiently low that, if the viscous composition comprises any bioactive factors, the bioactive factors will not undergo heat-induced degradation.

4. The method as in claim 1, wherein the using a viscous composition to form the three-dimensional object step further comprises:
   before the hydrating step, extruding the viscous composition through a nozzle to form an extruded composition, the extruded composition forming one or more fibers and drying the one or more fibers to form the three-dimensional object without any additional chemical, physical, or thermal processing.

5. The method as in claim 4, wherein the using a viscous composition to form the three-dimensional object, including extruding the viscous composition, is performed at temperatures that are sufficiently low that, if the viscous composition comprises any bioactive factors, the bioactive factors will not undergo heat-induced degradation.

6. The method as in claim 4, wherein extruding the viscous composition further comprises:
   a step of depositing the one or more extruded fibers in a printed layer.

7. The method as in claim 6, wherein the three-dimensional object comprises multiple, vertically stacked printed layers, by performing the depositing step repeatedly;

wherein repeating the depositing step comprises forming subsequently printed layers on top of previously formed printed layers, and each of the subsequently printed layers bonding to at least one of the previously formed printed layer on which that subsequently printed layer is deposited.

8. The method as in claim 1, further comprising:
after the dissolving step, drying the porous material system to remove moisture.

9. The method as in claim 1, further comprising:
after the dissolving step, sintering the porous material system.

10. The method as in claim 1, further comprising:
back-filling pores in the porous material system with a liquid solution or a hydrogel.

11. The method as in claim 10, wherein the liquid solution or the hydrogel has biological cells, bioactive factors, or a combination thereof, dispersed therein.

12. The method as in claim 1, further comprising:
seeding the porous material system with biological cells and culturing the biological cell-seeded porous material system in a cell culture medium.

13. The method as in claim 1, the viscous composition further comprising bioactive factors.

14. The method as in claim 1, wherein the salt-hydrating solution is an alcohol-water solution.

15. The method as in claim 1, wherein the viscous composition comprises a viscosity of 1 to 100 pascal seconds.

16. The method as in claim 1, wherein the viscous composition comprises a viscosity of 25 to 100 pascal seconds.

17. The method as in claim 1, wherein the viscous composition comprises a viscosity of 25 to 50 pascal seconds.

18. The method as in claim 1, wherein the viscous composition comprises a viscosity of 1 to 5 pascal seconds.

19. The method as in claim 1, wherein the three-dimensional object is formed from the viscous composition using one or more of extrusion, 3D-printing, additive manufacturing, coating, molding, casting, and electrospinning.

20. The method as in claim 1, wherein the three-dimensional object is formed from the viscous composition by evaporation of a solvent of the viscous composition.

* * * * *

UNITED STATES PATENT AND TRADEMARK OFFICE
CERTIFICATE OF CORRECTION

PATENT NO. : 11,896,740 B2
APPLICATION NO. : 16/760355
DATED : February 13, 2024
INVENTOR(S) : Adam E. Jakus, Ramille N. Shah and Nicholas R. Geisendorfer It is certified that error appears in the above-identified patent and that said Letters Patent is hereby corrected as shown below:

In the Specification

Column 3, Line 7, where the phrase "EthanolFirst" should be replaced with "Ethanol First".

Column 3, Line 27, where the phrase "EthanolFirst" should be replaced with "Ethanol First".

Column 11, Line 67, where the phrase "(30-35 Pa s)" should be replaced with "(30-35 Pa·s)".

Column 12, Line 38, where the phrase "200 urn" should be replaced with "200 µm".

Column 18, Line 47, where the phrase "which is 95% porous" should be replaced with "which is ~95% porous".

Column 21, Line 14, where the phrase "for -24 hours" should be replaced with "for ~24 hours".

Signed and Sealed this
Second Day of April, 2024

Katherine Kelly Vidal
*Director of the United States Patent and Trademark Office*